US011773064B2

(12) United States Patent
Papeo et al.

(10) Patent No.: US 11,773,064 B2
(45) Date of Patent: *Oct. 3, 2023

(54) 4-CARBOXAMIDO-ISOINDOLINONE DERIVATIVES AS SELECTIVE PARP-1 INHIBITORS

(71) Applicant: NERVIANO MEDICAL SCIENCES S.R.L., Nerviano (IT)

(72) Inventors: Gianluca Mariano Enrico Papeo, Cernusco Lombardone (IT); Mikhail Yurievitch Krasavin, Nathan (AU); Paolo Orsini, Legnano (IT); Alessandra Scolaro, Bresso (IT)

(73) Assignee: NERVIANO MEDICAL SCIENCES S.R.L., Nerviano (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/863,941

(22) Filed: Jul. 13, 2022

(65) Prior Publication Data
US 2022/0363636 A1    Nov. 17, 2022

Related U.S. Application Data

(60) Continuation of application No. 17/018,504, filed on Sep. 11, 2020, now Pat. No. 11,420,940, which is a continuation of application No. 16/460,438, filed on Jul. 2, 2019, now Pat. No. 10,800,739, which is a division of application No. 14/438,410, filed as application No. PCT/EP2013/072165 on Oct. 23, 2013, now Pat. No. 10,385,018.

(30) Foreign Application Priority Data

Oct. 26, 2012  (EP) .................... 12190130

(51) Int. Cl.

| | |
|---|---|
| *A61K 31/4035* | (2006.01) |
| *C07D 209/44* | (2006.01) |
| *C07D 401/06* | (2006.01) |
| *C07D 209/46* | (2006.01) |
| *C07D 401/14* | (2006.01) |
| *C07D 403/02* | (2006.01) |
| *C07D 403/04* | (2006.01) |
| *C07D 403/14* | (2006.01) |
| *C07D 405/04* | (2006.01) |
| *C07D 405/14* | (2006.01) |
| *C07D 407/14* | (2006.01) |
| *C07D 409/14* | (2006.01) |
| *C07D 413/06* | (2006.01) |
| *C07D 413/14* | (2006.01) |
| *A61K 31/4188* | (2006.01) |
| *A61K 31/4439* | (2006.01) |
| *A61K 31/454* | (2006.01) |
| *A61K 31/4725* | (2006.01) |
| *A61K 31/496* | (2006.01) |
| *A61K 31/5377* | (2006.01) |

(52) U.S. Cl.
CPC ........ *C07D 209/44* (2013.01); *A61K 31/4035* (2013.01); *A61K 31/4188* (2013.01); *A61K 31/4439* (2013.01); *A61K 31/454* (2013.01); *A61K 31/4725* (2013.01); *A61K 31/496* (2013.01); *A61K 31/5377* (2013.01); *C07D 209/46* (2013.01); *C07D 401/06* (2013.01); *C07D 401/14* (2013.01); *C07D 403/02* (2013.01); *C07D 403/04* (2013.01); *C07D 403/14* (2013.01); *C07D 405/04* (2013.01); *C07D 405/14* (2013.01); *C07D 407/14* (2013.01); *C07D 409/14* (2013.01); *C07D 413/06* (2013.01); *C07D 413/14* (2013.01)

(58) Field of Classification Search
CPC .................................. A61K 31/4035
See application file for complete search history.

(56) References Cited

U.S. PATENT DOCUMENTS

| | | |
|---|---|---|
| 7,232,842 B2 | 6/2007 | Wender et al. |
| 8,765,972 B2 | 7/2014 | Papeo et al. |
| 8,877,944 B2 | 11/2014 | Papeo et al. |

(Continued)

FOREIGN PATENT DOCUMENTS

| | | | |
|---|---|---|---|
| WO | 2007/047646 A2 | 4/2007 | |
| WO | 2010/133647 A1 | 11/2010 | |
| WO | 2011/006794 A1 | 1/2011 | |
| WO | 2011/006803 A1 | 1/2011 | |
| WO | WO-2014064149 A1 * | 5/2014 | ......... A61K 31/4035 |

OTHER PUBLICATIONS

Wesolowski "Temozolomide (Temodar)"AJNR Am J Neuroradiol 31:1383-84 Sep. 2010 1383-1384.*
Bissery MC et al., "Experimental Antitumor Activity and Pharmacokinetics of the Camptothecin Analog Irinotecan (CPT-11) in Mice" Anti-Cancer Drugs 7:437-460 (1996).
Collins P.W. et al., "18-Cycloalkyl Analogues of Enisoprost", Journal of Medicinal Chemistry 32(5):1001-1006 (1989).
Damia G. et al., "Contemporary Pre-Clinical Development of Anticancer Agents-What are the Opitmal Preclinical Models?", European Journal of Cancer 45:2768-2781 (2009).

(Continued)

*Primary Examiner* — David K O'Dell
(74) *Attorney, Agent, or Firm* — Scully, Scott, Murphy & Presser, P.C.

(57) ABSTRACT

There are provided substituted 4-carboxamido-isoindolinone derivatives which selectively inhibit the activity of poly (ADP-ribose) polymerase PARP-I with respect to poly (ADP-ribose) polymerase P ARP-2. The compounds of this invention are therefore useful in treating diseases such as cancer, cardiovascular diseases, central nervous system injury and different forms of inflammation. The present invention also provides methods for preparing these compounds, pharmaceutical compositions comprising these compounds, and methods of treating diseases utilizing pharmaceutical compositions comprising these compounds.

6 Claims, No Drawings

(56) References Cited

U.S. PATENT DOCUMENTS

| | | | |
|---|---|---|---|
| 10,385,018 | B2 | 8/2019 | Papeo et al. |
| 10,800,739 | B2 | 10/2020 | Papeo et al. |
| 2008/0108659 | A1 | 5/2008 | Gandhi et al. |
| 2015/0274662 | A1 | 10/2015 | Papeo et al. |
| 2019/0330151 | A1 | 10/2019 | Papeo et al. |
| 2020/0407314 | A1 | 12/2020 | Papeo et al. |

OTHER PUBLICATIONS

Gandhi V.B. et al., "Discovery and SAR of Substituted 3-Oxoisoindoline-4-Carboxamides as Potent Inhibitors of Poly(ADP-Ribose) Polymerase (PARP) for the Treatment of Cancer", Bioorganic & Medicinal Chemistry Letters 20:1023-1026 (2010).

Kummar S. et al., "Advances in Using PARP Inhibitors to Treat Cancer", BMC Medicine 10:25 (2012).

Lin K.Y. et al., "PARP Inhibitors for Cancer Therapy", Cell 169:183 (Apr. 6, 2017).

Menear K.A. et al., "4-[3-(4-Cyclopropanecarbonylpiperazine-1-Carbonyl)-4-Fluorobenzyl]-2H-Phthalazin-1-One: A Novel Bioavailable Inhibitor of Poly(ADP-Ribose) Polymerase-1", Journal of Medicinal Chemistry 51(20):6581-6591 (2008).

Ocana A. et al., "Preclinical Development of Molecular-Targeted Agents for Cancer", Nature Reviews:Clinical Oncolgy 8:200-209 (Apr. 2011).

Sabater S. et al., "Hydrodefluorination of Carbon-Fluorine Bonds by the Synergistic Action of a Ruthenium-Palladium Catalyst", Nature Communications 4(2553):1-7 (2013).

Sharma S.V. et al., "Cell Line-Based Platforms to Evaluate the Therapeutic Efficacy of Candidate Anticancer Agents", Nature Reviews: Cancer 10:241-253 (Apr. 2010).

Simeoni M. et al., "Predictive Pharmacokinetic-Pharmacodynamic Modeling of Tumor Growth Kinetics in Xenograft Models After Administration of Anticancer Agents", Cancer Research 64:1094-1101 (Feb. 1, 2004).

Yelamos J. et al., "PARP-1 and PARP-2: New Players in Tumour Development", Am J Cancer Res 1(3):328-346 (2011).

Committee for Orphan Medicinal Products, Public Summary of Opinion on Orphan Designation-Olaparib for the Treatment of Ovarian Cancer, European Medicines Agency (Mar. 3, 2015).

International Search Report dated Mar. 7, 2014 received in International Application No. PCT/EP2013/072165.

\* cited by examiner

4-CARBOXAMIDO-ISOINDOLINONE DERIVATIVES AS SELECTIVE PARP-1 INHIBITORS

CROSS-REFERENCE TO RELATED APPLICATIONS

The present application is a continuation of co-pending application having U.S. Ser. No. 17/018,5045, filed on Sep. 11, 2020, which is a continuation of co-pending application having U.S. Ser. No. 16/460,438, filed on Jul. 2, 2019, now U.S. Pat. No. 10,800,739, which is a divisional of co-pending application having U.S. Ser. No. 14/438,410, filed on Apr. 24, 2015, now U.S. Pat. No. 10,385,018 B2, which is a 371 of International Application having Serial No. PCT/EP2013/072165, filed on Oct. 23, 2013, which claims benefit of European Patent Application No. 12190130.0, filed on Oct. 26, 2012, the contents of all of which are incorporated herein by reference.

The present invention provides novel substituted 4-carboxamido-isoindolinone derivatives which proved to be potent and selective poly (ADP-ribose) polymerase-1 (PARP-1) inhibitors with respect to poly (ADP-ribose) polymerase-2 (PARP-2) and are thus useful in the therapy of cancer, cardiovascular diseases, nervous system injury and inflammation. The present invention also provides methods for preparing these compounds, pharmaceutical compositions comprising these compounds, and methods of treating diseases utilizing pharmaceutical compositions comprising these compounds.

Poly (ADP-ribose) polymerases belong to a family of 18 members that catalyze the addition of ADP-ribose units to DNA or different acceptor proteins, which affect cellular processes as diverse as replication, transcription, differentiation, gene regulation, protein degradation and spindle maintenance. PARP-1 and PARP-2 are the only enzymes among the PARPs that are activated by DNA damage and are involved in DNA repair.

PARP-1 is a nuclear protein consisting of three domains: the N-terminal DNA-binding domain containing two zinc fingers, the auto modification domain, and the C-terminal catalytic domain. PARP-1 binds through the zinc-finger domain to DNA single strand breaks (SSB), cleaves $NAD^+$, and attaches multiple ADP-ribose units to target proteins such as histones and various DNA repair enzymes. This results in a highly negatively charged target, which in turn leads to the unwinding and repair of the damaged DNA through the base excision repair pathway. In knock out mouse models, deletion of PARP-1 impairs DNA repair but it is not embryonic lethal. Double knock out PARP-1 and PARP-2 mice instead die during early embryogenesis, suggesting that the two enzymes display not completely overlapping functions. Enhanced PARP-1 expression and/or activity have been shown in different tumor cell lines, including malignant lymphomas, hepatocellular carcinoma, cervical carcinoma, colorectal carcinoma, leukemia. This may allow tumor cells to withstand genotoxic stress and increase their resistance to DNA-damaging agents. As a consequence, inhibition of PARP-1 through small molecules has been shown to sensitize tumor cells to cytotoxic therapy (e.g. temozolomide, platinums, topoisomerase inhibitors and radiation). A significant window seems to exist between the ability of a PARP inhibitor to potentiate therapeutic benefits and undesirable side effects. Whereas the therapeutic use of PARP inhibitors in combination with DNA damaging agents is not novel, the use of these agents as monotherapy, in particular tumor genetic backgrounds deficient in the homologous recombination DNA repair, represents a new approach. Individuals with heterozygous germ line mutations in either the BRCA-1 or BRCA-2 homologous recombination repair genes exhibit high life time risks of developing breast and other cancers. Tumors arising in mutation carriers have generally lost the wild type allele and do not express functional BRCA-1 and BRCA-2 proteins.

Therefore, loss of these two proteins leads to a tumor-specific dysfunction in the repair of double strand breaks by homologous recombination. It is known that when PARP-1 is inhibited, base excision repair is reduced and single strand breaks that are generated during the normal cell cycle persist. It has also been established that replication forks that encounter an unrepaired break can form double strand breaks which are normally repaired by homologous recombination. Tumor cells that are deficient in homologous recombination repair such as BRCA-1 and BRCA-2 mutants are therefore highly sensitive to PARP inhibition compared with wild-type cells. This is in line with the concept of synthetic lethality, in which the two pathway defects alone are innocuous but combined become lethal: PARP inhibitors may be more effective in patients with tumors with specific DNA repair defects without affecting normal heterozygous tissues. Putative patient population includes, besides BRCA mutants that represent the majority of hereditary breast and ovarian cancer, also a substantial fraction of sporadic cancers with defects in homologous recombination repair, a phenomenon termed 'BRCAness'. For example, methylation of the promoters of the BRCA-1 or FANCF genes and amplification of the EMSY gene, which encodes a BRCA-2 interacting protein. By extending the rational of synthetic lethality of PARP and BRCA-1 and BRCA-2, it is likely that deficiencies in any gene that is not redundant in double strand break repair should be sensitive to PARP inhibition. For example, ATM deficiency, found in patients with T-cell prolymphocytic leukemia and B-cell chronic lymphocytic leukemia and breast cancer and CHK2 germ line mutations identified in sarcoma, breast cancer, ovarian cancer and brain tumors, have also been shown to be synthetically lethal in combination with PARP deficiency as well as deficiencies in other known HR pathway proteins (including RAD51, DSS1, RAD54, RPA1, NBS1, ATR, CHK1, CHK2, FANCD2, FANCA, FANCC and pTEN). Mutations in FANCC and FANCG have been shown in pancreatic cancer. Methylation of FANCF promoter has been found in ovarian, breast, cervical, lung carcinomas. The first clinical evidence that BRCA-mutated cancer may be sensitive to PARP inhibitor monotherapy comes from the phase I trial of the oral, small molecule PARP inhibitor Olaparib. In an enriched phase I population for BRCA mutation carriers, an objective response rate of 47% were observed in 19 patients with BRCA mutations and breast, ovarian and prostate cancer. Other PARP inhibitors, such as Rucaparib and Veliparib are currently known to be in phase II clinical trials in combination as well as single agent. Early indications are that these therapies show low toxicity as single agent. Anyway compounds with high selectivity on PARP-1 are expected to show even less toxicity in view of a chronic treatment schedule or in combination.

PARP-1 has also been implicated in angiogenesis. In particular, PARP-1 inhibition seems to result in decreased accumulation of the transcription hypoxia-inducible factor 1, an important regulator of tumor cell adaptation to hypoxia.

Pro-inflammatory stimuli trigger the release of pro-inflammatory mediators that induce the production of peroxynitrate and hydroxyl radicals, which in turn yield to DNA single strand breakage with consequent activation of PARP-1. Over activation of PARP-1 results in depletion of NAD+ and energy stores, culminating in cell dysfunction and necrosis. This cellular suicide mechanism has been implicated in the pathomechanism of stroke, myocardial ischemia, diabetes, diabetes-associated cardiovascular dysfunction, shock, traumatic central nervous system injury, arthritis, colitis, allergic encephalomyelitis and various other forms of inflammation. Of special interest is the enhancement by PARP-1 of nuclear factor kB-mediated transcription, which plays a central role in the expression of inflammatory cytokines, chemokines and inflammatory mediators.

WO 2007/047646 in the name of Janssen Pharmaceutica describes substituted dihydro-isoindolones useful for treating kinase disorders; Wender et al. claim in U.S. Pat. No. 7,232,842 isoindolone analogs as kinase inhibitors. The Patent Application US 2008/0108659 of Gandhi et al. describes 3-oxo-2,3-dihydro-1H-isoindoles as poly (ADP-ribose) polymerase inhibitors, also reported in: *Bioorg. Med. Chem. Lett.*, 2010, 20, 1023-1026. WO 2011/006794 and WO 2011/006803, both in the name of Nerviano Medical Sciences, describe 3-oxo-2,3-dihydro-1H-isoindole-4-carboxamides as selective PARP-1 inhibitors.

The present invention provides novel substituted 4-carboxamido-isoindolinone derivatives which proved to be potent and selective PARP-1 inhibitors with respect to PARP-2 and are thus useful in the therapy of cancer, cardiovascular diseases, nervous system injury and inflammation.

The present invention also provides method for preparing these compounds, pharmaceutical compositions comprising these compounds, and methods of treating diseases utilizing pharmaceutical compositions comprising these compounds.

Accordingly, a first object of the present invention is to provide a compound of formula (I):

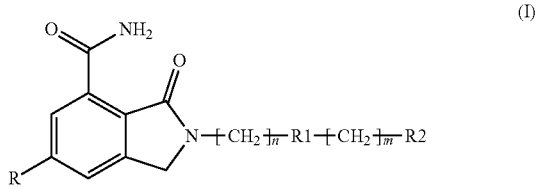

(I)

wherein:

R is hydrogen or fluorine; and n, m, R1 and R2 have the following meanings:

a) n is 0 and m is 0, 1, 2 or 3;

R1 is 3- to 6-membered cycloalkyl or 4- to 6-membered heterocycyl; and

R2 is a 3-, 5- or 6-membered cycloalkyl, 4- to 6-membered heterocyclyl, aryl or heteroaryl; or b) n is 1 and m is 0:

R1 is 3- to 6-membered cycloalkyl or aryl, each of which optionally further substituted with one or more linear or branched $(C_1$-$C_6)$-alkyl; and R2 is null, 3- to 6-membered cycloalkyl, 4- to 6-membered heterocyclyl, aryl or heteroaryl, each of which optionally further substituted with one or more linear or branched $(C_1$-$C_6)$-alkyl;

or c) n is 2 or 3, and m is 0;

R1 is a 3- to 6-membered cycloalkyl, 4- to 6-membered heterocyclyl, aryl or heteroaryl, each of which optionally further substituted with one or more linear or branched $(C_1$-$C_6)$-alkyl; and R2 is null, 3- to 6-membered cycloalkyl, 4- to 6-membered heterocycyl, aryl or heteroaryl, each of which optionally further substituted with one or more linear or branched $(C_1$-$C_6)$-alkyl;

or d) n and m are each independently 1, 2 or 3;

R1 and R2 are each independently 3- to 6-membered cycloalkyl, 4- to 6-membered heterocycyl, aryl or heteroaryl; or a pharmaceutically acceptable salt thereof.

The compounds of formula (I) as defined above are potent and selective PARP-1 inhibitors with respect to PARP-2 and are thus useful in cancer, cardiovascular diseases, nervous system injury and inflammation therapy.

The present invention also provides methods of synthesizing substituted 4-carboxamido-isoindolinone derivatives of formula (I) as defined above, through a process consisting of standard synthetic transformations.

The present invention also provides a method for treating diseases mediated by PARP-1 protein which comprises administering to a mammal in need thereof, preferably a human, an effective amount of a compound of formula (I), as defined above.

A preferred method of the present invention is to treat a disease mediated by PARP-1 protein selected from the group consisting of cancer, cardiovascular diseases, nervous system injury and inflammation.

Another preferred method of the present invention is to treat specific types of cancer including, but not limited to: carcinomas, such as bladder, breast, colon, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukemia; tumors of mesenchymal origin, including fibrosarcoma, Ewing's sarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xeroderma pigmentosum, keratoxanthoma, thyroid follicular cancer and Kaposi's sarcoma.

In addition, the method of the present invention also provides tumor angiogenesis and metastasis inhibition.

Another preferred method of the present invention is to treat specific types of cardiovascular diseases including, but not limited to, myocardial reperfusion injury, cardiomyopathy, diabetic cardiovascular dysfunction.

Another preferred method of the present invention is to treat specific types of nervous system injury including but not limited to: stroke, brain injury and neurodegenerative disorders.

Another preferred method of the present invention is to treat specific types of inflammation diseases including, but not limited to, colitis, arthritis and uveitis.

The present invention also provides an in vitro method for selectively inhibiting PARP-1 protein activity which comprises contacting the said protein with an effective amount of a compound of formula (I), as defined above.

The present invention further provides a method for treating diseases comprising a compound of formula (I), as defined above, in combination with radiation therapy or chemotherapy regimen for simultaneous, separate or sequential use in anticancer therapy.

The present invention also provides a pharmaceutical composition comprising a therapeutically effective amount of a compound of formula (I) or a pharmaceutically acceptable salt thereof, as defined above, and at least one pharmaceutically acceptable excipient, carrier or diluent.

In addition to a compound of formula (I), the pharmaceutical composition of the present invention may further comprise one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrix metalloproteinases inhibitors, telomerase inhibitors, tyrosine kinase inhibitors, anti-growth factor receptor agents, anti-HER agents, anti-EGFR agents, antimangiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhbitors, topoisomerase II inhibitors, and the like. Preferably, the chemotherapeutic agent is an alkylating agent. Even more preferably, the alkylating agent is temozolomide.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy. Preferably, the chemotherapeutic agent is an alkylating agent. Even more preferably, the alkylating agent is temozolomide.

Moreover, the invention provides a compound of formula (I) or a pharmaceutically acceptable salt thereof, as defined above, for use as a medicament, preferably as a medicament with anticancer activity.

In yet another aspect, the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

The compounds of formula (I) may have one or more asymmetric centers, and may therefore exist as individual optical isomers or racemic mixtures or diastereoisomers. Accordingly, all the possible isomers, and their mixtures of the compounds of formula (I) are within the scope of the present invention. As stated above, salts of the compounds of formula (I) are also within the scope of the present invention.

Unless otherwise specified, when referring to the compounds of formula (I) per se as well as to any pharmaceutical composition thereof or to any therapeutic treatment comprising them, the present invention includes all of the isomers, tautomers, hydrates, solvates, N-oxides and pharmaceutically acceptable salts of the compounds of this invention.

If a chiral center or another form of an isomeric center is present in a compound of the present invention, all forms of such isomer or isomers, including enantiomers and diastereoisomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

With the term "halogen" we intend a fluorine, chlorine, bromine or iodine atom.

With the term "linear or branched $(C_1-C_6)$-alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "3- to 6-membered cycloalkyl" we intend, unless otherwise provided, a 3- to 6-membered all-carbon monocyclic ring, which may contain one or more double bonds but does not have a completely conjugated π-electron system. Examples of cycloalkyl groups, without limitation, are cyclopropyl, cyclobutyl, cyclopentyl, cyclopentenyl, cyclohexyl, cyclohexenyl and cyclohexadienyl.

With the term "4- to 6-membered heterocyclyl" we intend a 4- to 6-membered, saturated or partially unsaturated carbocylic ring where one or more carbon atoms are replaced by heteroatoms such as nitrogen, oxygen and sulfur; the heterocyclyl ring can be optionally further fused or linked to aromatic and non-aromatic carbocyclic and heterocyclic rings. Non limiting examples of heterocyclyl groups are, for instance, pyranyl, pyrrolidinyl, pyrrolinyl, imidazolinyl, imidazolidinyl, pyrazolidinyl, pyrazolinyl, thiazolinyl, thiazolidinyl, dihydrofuranyl, tetrahydrofuranyl, 1,3-dioxolanyl, piperidinyl, piperazinyl, morpholinyl and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated T-electron bond system. Non limiting examples of such aryl groups are phenyl, α- or β-naphthyl or biphenyl groups.

The term "heteroaryl" refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, indazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the present invention and unless otherwise provided, when any of the above mentioned groups is optionally substituted, it may be substituted in any of its free position by one or more linear or branched $(C_1-C_6)$ alkyl groups.

The term "pharmaceutically acceptable salt" of compounds of formula (I) refers to those salts that retain the biological effectiveness and properties of the parent compound, therefore pharmaceutically acceptable salts of the compounds of formula (I) include the acid addition salts with inorganic or organic acids, e.g., nitric, hydrochoric, hydrobromic, sulfuric, perchloric, phosphoric, acetic, trifluoroacetic, propionic, glycolic, (D) or (L) lactic, oxalic, ascorbic, fumaric, malonic, malic, maleic, tartaric, citric, benzoic, cinnamic, mandelic, methanesulphonic, ethanesulfonic, p-toluenesulfonic, isethionic, succinic and salicylic acid.

Pharmaceutically acceptable salts of the compounds of formula (I) also include the salts with inorganic or organic bases, e.g., alkali or alkaline-earth metals, especially sodium, potassium, calcium, ammonium or magnesium hydroxides, carbonates or bicarbonates, and acyclic or cyclic amines, preferably methylamine, ethylamine, diethylamine, triethylamine, piperidine and the like.

In a first preferred embodiment, the present invention provides compounds of formula (I) as defined above characterized in that
R is hydrogen or fluorine; and
n, m, R1 and R2 have the following meanings:
a) n is 0 and m is 0 or 1;
R1 is a 6-membered heterocycyl; and
R2 is a 3- or 6-membered cycloalkyl, 6-membered heterocycyl, aryl or heteroaryl;
or
b) n is 1 and m is 0;
R1 is aryl, optionally further substituted with one or more linear or branched ($C_1$-$C_6$)-alkyl; and
R2 is null;
or
c) n is 2 or 3, and m is 0;
R1 is a 6-membered heterocycyl, aryl or heteroaryl, each of which optionally further substituted with one or more linear or branched ($C_1$-$C_6$)-alkyl; and
R2 is null, a 6-membered heterocycyl or aryl;
or
d) n is 2 or 3, and m is 1;
R1 is a 6-membered heterocycyl; and
R2 is aryl;
or a pharmaceutically acceptable salt thereof.

In a more preferred embodiment, the present invention provides compounds of formula (I) as defined above characterized in that
R is hydrogen or fluorine; and
n, m, R1 and R2 have the following meanings:
a) n is 0 and m is 0 or 1;
R1 is a 6-membered heterocycyl; and
R2 is a 3- or 6-membered cycloalkyl, 6-membered heterocycyl, aryl or heteroaryl;
or
c) n is 2 or 3, and m is 0;
R1 is a 6-membered heterocyclyl, aryl or heteroaryl, each of which optionally further substituted with one or more linear or branched ($C_1$-$C_6$)-alkyl; and
R2 is null, a 6-membered heterocycyl or aryl;
or a pharmaceutically acceptable salt thereof.

Even more preferably, the present invention provides compounds of formula (I) as defined above characterized in that
R is hydrogen or fluorine; and
n, m, R1 and R2 have the following meanings:
a) n is 0 and m is 0 or 1;
R1 is a 6-membered heterocycyl; and
R2 is a 3- or 6-membered cycloalkyl, 6-membered heterocycyl, aryl or heteroaryl;
or a pharmaceutically acceptable salt thereof.

Most preferably, the present invention provides compounds of formula (I) as defined above characterized in that
R is hydrogen or fluorine; and
n, m, R1 and R2 have the following meanings:
a) n is 0 and m is 0 or 1;
when m is 0, R1 is a piperidine ring and R2 is a cyclohexyl ring;
when m is 1, R1 is a piperidine ring and R2 is a pyridine ring;
or a pharmaceutically acceptable salt thereof.

Specific preferred compounds (cpd) of the present invention are listed below:
1. 2-benzyl-3-oxo-2,3-dihydro-1H-isoindole-4-carboxylic acid amide;
2. 3-oxo-2-phenethyl-2,3-dihydro-1H-isoindole-4-carboxylic acid amide;
3. 2-[2-(3,4-dihydro-1H-isoquinolin-2-yl)-ethyl]-3-oxo-2,3-dihydro-1H-isoindole-4-carboxylic acid amide;
4. 3-oxo-2-(2-piperidin-1-yl-ethyl)-2,3-dihydro-1H-isoindole-4-carboxylic acid amide;
5. 2-(2-morpholin-4-yl-ethyl)-3-oxo-2,3-dihydro-1H-isoindole-4-carboxylic acid amide;
6. 2-(3-morpholin-4-yl-propyl-3-oxo-2,3-dihydro-1H-isoindole-4-carboxylic acid amide;
7. 2-[2-(3,4-dihydro-2H-quinolin-1-yl-ethyl]-3-oxo-2,3-dihydro-1H-isoindole-4-carboxylic acid amide;
8. 3-oxo-2-(1-pyridin-4-ylmethyl-piperidin-4-yl)-2,3-dihydro-1H-isoindole-4-carboxylic acid amide;
9. 3-oxo-2-(1-thiophen-2-ylmethyl-piperidin-4-yl)-2,3-dihydro-1H-isoindole-4-carboxylic acid amide;
10. 3-oxo-2-(1-pyridin-3-ylmethyl-piperidin-4-yl)-2,3-dihydro-1H-isoindole-4-carboxylic acid amide;
11. 2-(1-cyclohexyl-piperidin-4-yl)-3-oxo-2,3-dihydro-1H-isoindole-4-carboxylic acid amide;
12. 2-(1-furan-2-ylmethyl-piperidin-4-yl)-3-oxo-2,3-dihydro-1H-isoindole-4-carboxylicacid amide;
13. 3-oxo-2-(1-thiophen-3-ylmethyl-piperidin-4-yl)-2,3-dihydro-1H-isoindole-4-carboxylicacid amide;
14. 2-(1-furan-3-ylmethyl-piperidin-4-yl)-3-oxo-2,3-dihydro-1H-isoindole-4-carboxylic acid amide;
15. 3-oxo-2-(1-pyridin-2-ylmethyl-piperidin-4-yl)-2,3-dihydro-1H-isoindole-4-carboxylic acid amide;
16. 3-oxo-2-[1-(1H-pyrrol-2-ylmethyl)-piperidin-4-yl]-2,3-dihydro-1H-isoindole-4-carboxylic acid amide;
17. 3-oxo-2-(3-phenyl-propy)-2,3-dihydro-1H-isoindole-4-carboxylic acid amide;
18. 3-oxo-2-(2-pyridin-2-yl-ethyl)-2,3-dihydro-1H-isoindole-4-carboxylicacid amide;
19. 2-[3-(3,4-dihydro-1H-isoquinolin-2-yl)-propyl]-3-oxo-2,3-dihydro-1H-isoindole-4-carboxylicacid amide;
20. 2-[3-(3,4-dihydro-2H-quinolin-1-yl)-propyl]-3-oxo-2,3-dihydro-1H-isoindole-4-carboxylicacid amide;
21. 2-[3-(4-methyl-piperazin-1-yl)-propyl]-3-oxo-2,3-dihydro-1H-isoindole-4-carboxylic acid amide;
22. 3-oxo-2-[3-(4-phenyl-piperazin-1-yl)-propyl]-2,3-dihydro-1H-isoindole-4-carboxylic acid amide;
23. 6-fluoro-2-(3-morpholin-4-yl-propyl)-3-oxo-2,3-dihydro-1H-isoindole-4-carboxylic acid amide;
24. 2-(1-cyclopropylmethyl-piperidin-4-yl)-3-oxo-2,3-dihydro-1H-isoindole-4-carboxylic acid amide;
25. 3-oxo-2-(3-piperidin-1-yl-propyl)-2,3-dihydro-1H-isoindole-4-carboxylic acid amide;
26. 2-(3-[1,4']bipiperidinyl-1'-yl-propyl)-3-oxo-2,3-dihydro-1H-isoindole-4-carboxylic acid amide;
27. 2-[3-(2,6-dimethyl-piperidin-1-yl)-propyl]-3-oxo-2,3-dihydro-1H-isoindole-4-carboxylic acid amide;
28. 3-oxo-2-[1-(tetrahydro-pyran-4-yl)-piperidin-4-yl]-2,3-dihydro-1H-isoindole-4-carboxylic acid amide;
29. 2-(1-cyclohexyl-piperidin-4-yl)-6-fluoro-3-oxo-2,3-dihydro-1H-isoindole-4-carboxylic acid amide;
30. 2-(1-benzyl-piperidin-4-yl)-3-oxo-2,3-dihydro-1H-isoindole-4-carboxylic acid amide;
31. 2-[2-(1-benzyl-piperidin-4-yl)-ethyl]-3-oxo-2,3-dihydro-1-isoindole-4-carboxylic acid amide;
32. 2-[3-(4-benzyl-piperidin-1-yl)-propyl]-3-oxo-2,3-dihydro-1H-isoindole-4-carboxylic acid amide;

33. 2-[1-(4,4-dimethyl-cyclohexyl)-piperidin-4-yl]-3-oxo-2,3-dihydro-1H-isoindole-4-carboxylic acid amide;
34. 2-[1-(4,4-dimethyl-cyclohexyl-piperidin-4-yl]-6-fluoro-3-oxo-2,3-dihydro-1H-isoindole-4-carboxylic acid amide;
35. 6-fluoro-3-oxo-2-(1-spiro[2.5]oct-6-yl-piperidin-4-yl)-2,3-dihydro-1H-isoindole-4-carboxylic acid amide;
36. 3-oxo-2-(1-spiro[2.5]oct-6-yl-piperidin-4-yl)-2,3-dihydro-1H-isoindole-4-carboxylic acid amide;
or a pharmaceutically acceptable salt thereof.

The present invention also provides processes for the preparation of compounds of formula (I) as defined above. Accordingly, a process of the present invention comprises one of the following sequences of steps:

Sequence A (when R is Fluorine, Scheme 1):
either
Step a) halogenating 4-fluoro-2-methyl-phenylamine (X):

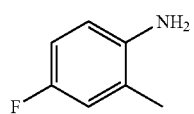
(XI)

Step b) cyano-de-aminating the resultant compound of formula (X):

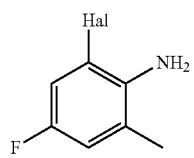
(X)

wherein Hal is halogen such as Cl, Br, and I;
Step c) hydrolyzing the resultant compound of formula (IX):

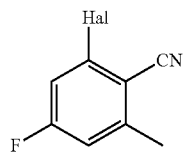
(IX)

wherein Hal is as defined above and
Step d) hydrolyzing the resultant compound of formula (VIII):

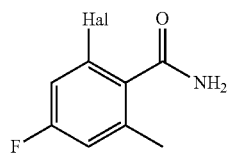
(VIII)

wherein Hal is as defined above;
or
Step e) halogenating 4-fluoro-2-methyl-benzoic acid (XII):

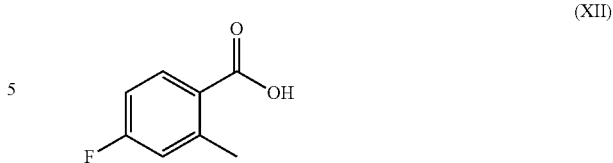
(XII)

Then:
Step f) esterifying the compound of formula (VII) obtained in step d) or e)

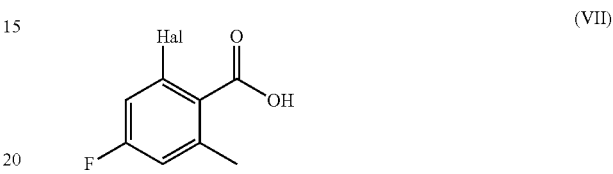
(VII)

wherein Hal is as defined above;
Step g) cyano-de-halogenating the resultant compound of formula (VI):

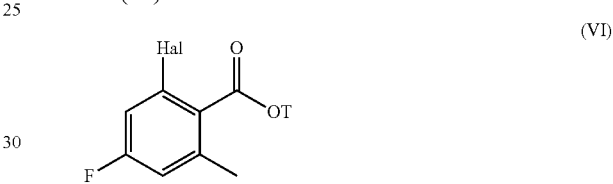
(VI)

wherein T is a $(C_1-C_6)$-alkyl or an aryl-$(C_1-C_6)$-alkyl and Hal is as defined above;
Step h) cyclizing the resultant compound of formula (V):

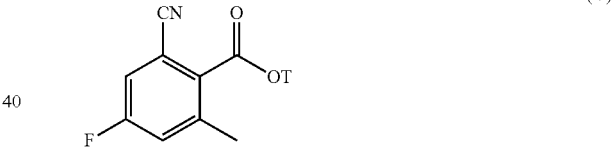
(V)

wherein T is as defined above, by reaction with a suitable amine of formula (XIII)

X—R1-[CH$_2$]$_n$—NH$_2$ (XIII)

wherein R1 and n are as defined above, and X is either R2-[CH$_2$]$_m$—, wherein R2 and m are as defined above, or a suitable nitrogen protective group, when R1 is a nitrogen containing heterocyclyl;
Step c') hydrolyzing the resultant compound of formula (IV):

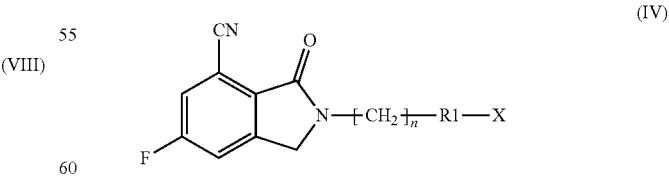
(IV)

wherein R1, n and X are as defined above, so as to obtain a compound of formula (I), as defined above, when X is R2-[CH$_2$]$_m$—, wherein R2 and m are as defined above; or a compound of formula (III), when R1 is a nitrogen containing heterocyclyl and X is a suitable nitrogen protective group, (III)

[Structure: fluorinated isoindolinone with carboxamide, N—(CH₂)ₙ—R1—X]

wherein n is as defined above, R1 is a nitrogen containing heterocyclyl and X is a suitable nitrogen protective group;

Step i) deprotecting the compound of formula (III), as defined above, so as to obtain either
a compound of formula (I), as defined above, or
a compound of formula (II):

(II)

[Structure: fluorinated isoindolinone with carboxamide, N—(CH₂)ₙ—R1—H]

wherein R1 and n are as defined above;

Step l) alkylating the resultant compound of formula (II), as defined above, with a suitable alkylating agent of formula (XIV)

R2-[CH₂]$_{m-1}$—Y     (XIV)

wherein Y is either a formyl group or, when m=1, an oxygen atom linked to R2 through a double bond (=O), so as to obtain a compound of formula (I).

Sequence B (when R is Hydrogen, Scheme 2):

Step m) performing a reductive amination on furan-2-carbaldehyde (XV):

(XV)

[Structure: furan-2-carbaldehyde]

with a suitable amine of formula (XIII)

X—R1-[CH₂]ₙ—NH₂     (XIII)

wherein R1 and n are as defined above, and X is either R2-[CH₂]$_m$—, wherein R2 and m are as defined above, or a suitable nitrogen protective group, when R1 is a nitrogen containing heterocyclyl;

Step n) performing a Diels-Alder reaction on the resultant compound of formula (XVI):

(XVI)

[Structure: furan with CH₂—NH—(CH₂)ₙ—R1—X]

wherein R1, n and X are as defined above;

Step o) aromatizing the resultant compound of formula (XVII):

(XVII)

[Structure: Diels-Alder bicyclic adduct with CO₂H and N—(CH₂)ₙ—R1—X]

wherein R1, n and X are as defined above;

Step p) amidating the resultant compound of formula (XVIII):

(XVIII)

[Structure: isoindolinone-carboxylic acid with N—(CH₂)ₙ—R1—X]

wherein R1, n and X are as defined above, so as to obtain
a compound of formula (I), as defined above, when X is R2-[CH₂]$_m$—, wherein R2 and m are as defined above; or
a compound of formula (XX), when R1 is a nitrogen containing heterocyclyl and X is a suitable nitrogen protective group, (XX)

[Structure: isoindolinone-carboxamide with N—(CH₂)ₙ—R1—X]

wherein n is as defined above, R1 is a nitrogen containing heterocyclyl and X is a suitable nitrogen protective group;

Step i') deprotecting a compound of formula (XX) as defined above;

Step l') alkylating the resultant compound of formula (XXI):

(XXI)

[Structure: isoindolinone-carboxamide with N—(CH₂)ₙ—R1—H]

wherein R1 and n are as defined above, with a suitable alkylating agent of formula (XIV)

R2-[CH]$_{m-1}$—Y     (XIV)

wherein Y is either a formyl group or, when m=1, an oxygen atom linked to R2 through a double bond (=O), so as to obtain a compound of formula (I), as defined above.

In case, during Step o, the compound resulting from aromatization of a compound of formula (XVI) is a compound of formula (XIX), i.e. when X is a labile nitrogen protective group, the following Step q is performed:

Step q) installing a suitable nitrogen protective group on the resultant compound of formula (XIX):

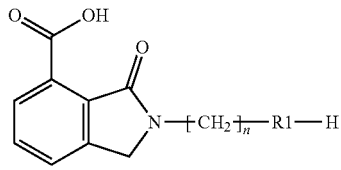
(XIX)

wherein R1 and n are as defined above, so as to obtain a compound of formula (XVIII), wherein R1 and n are as defined above and X is a suitable nitrogen protective group, which is then subjected to the sequence of reactions p), i') and l') above described so as to obtain a compound of formula (I) as above defined.

If necessary or wanted, the processes above described comprises converting a compound of formula (I) into a different compound of formula (I) by known chemical reactions; and/or, if desired, converting a compound of formula (I) into a pharmaceutically acceptable salt thereof or converting a salt into a free compound of formula (I).

Such known chemical reactions for possible conversions of compounds into different compounds comprise for instance a reductive amination (Cv1).

All the above processes are analogy processes which can be carried out according to well known methods and under suitable conditions known in the art.

The synthesis of a compound of formula (I), according to the synthetic processes described above, can be carried out in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

Schemes 1-2 below show the preparation of a compound of formula (I) as defined above.

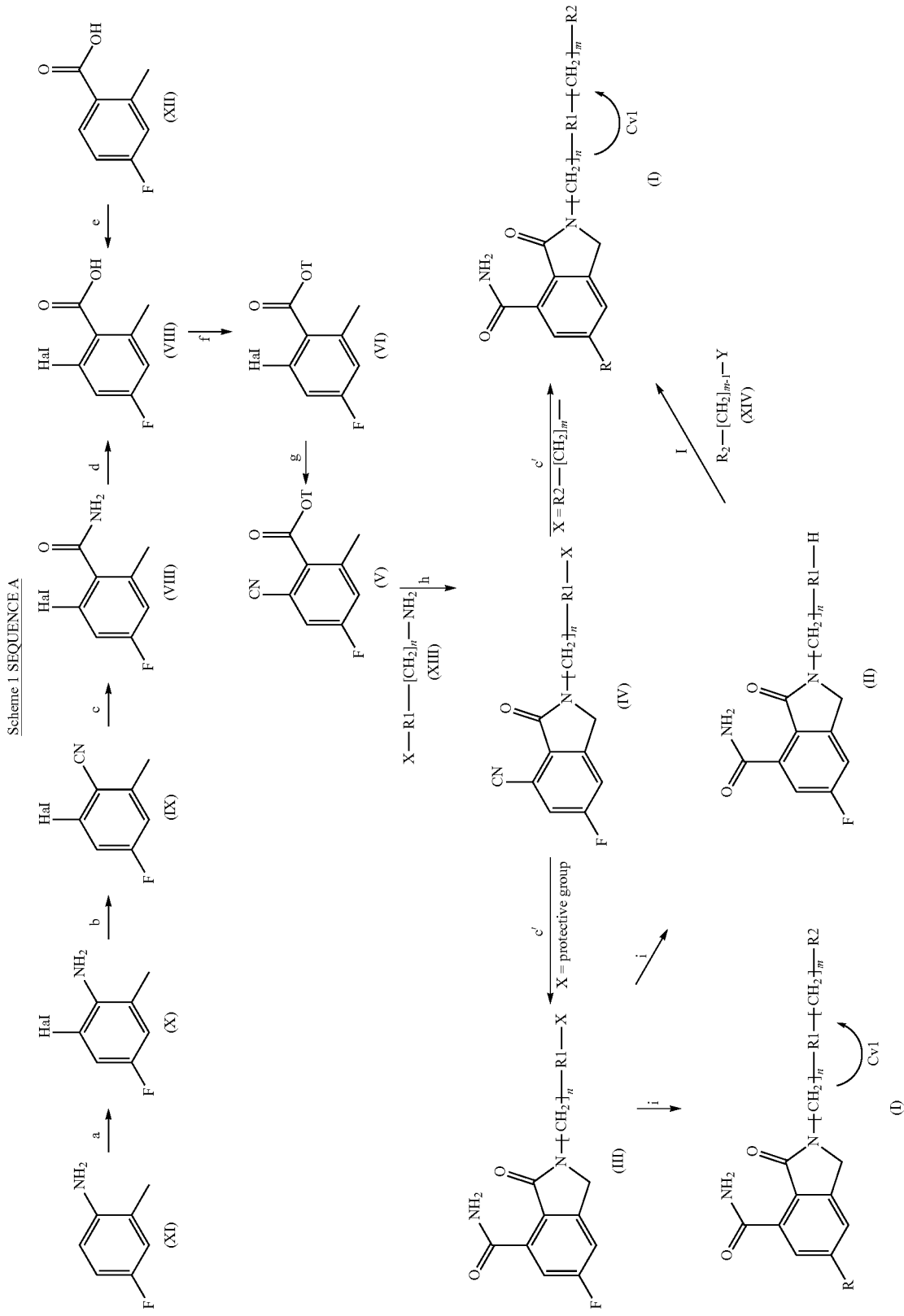

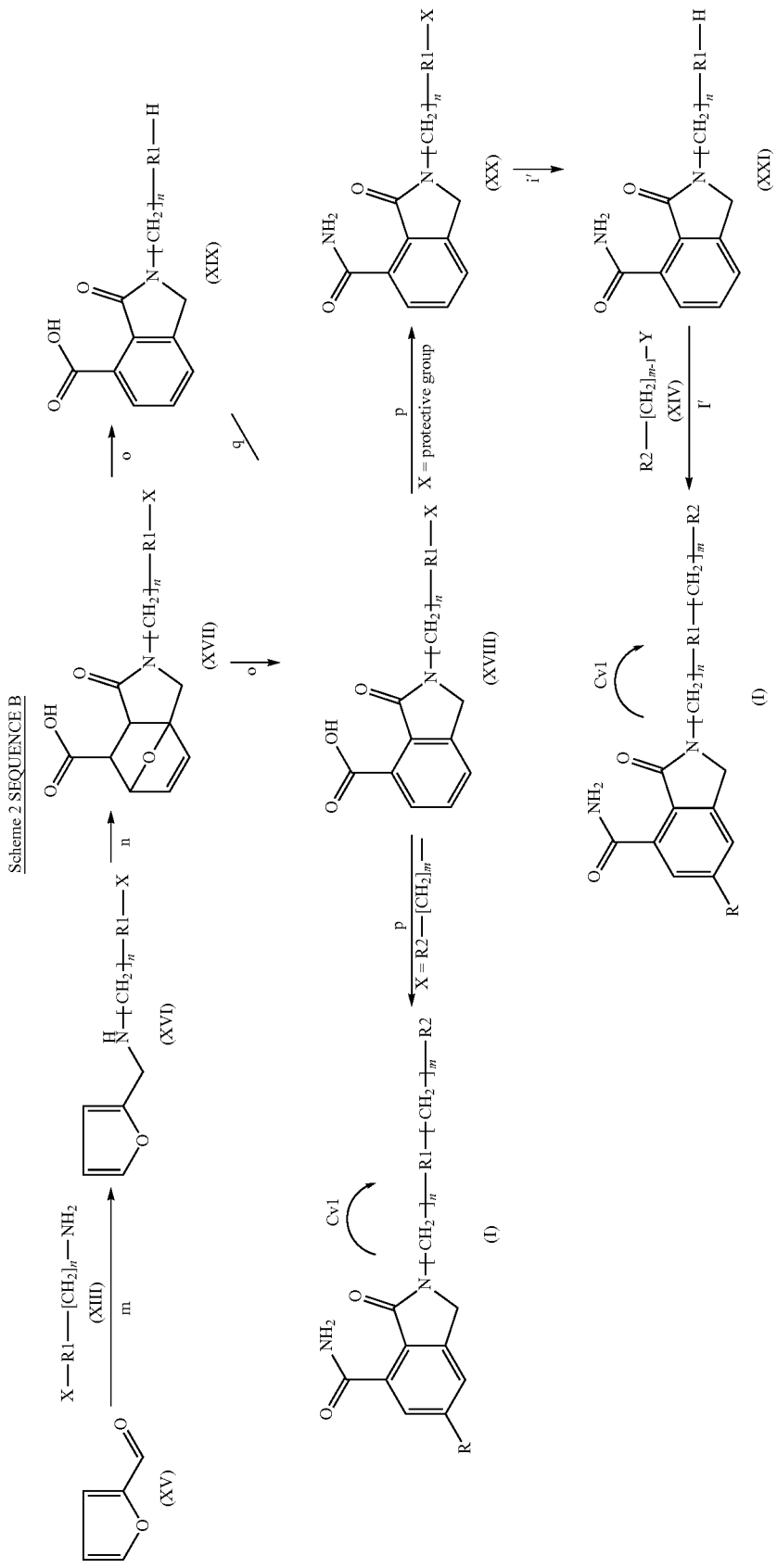

According to step a), a compound of formula (X) can be obtained by halogenating 4-fluoro-2-methyl-phenylamine (XI) in a variety of ways and experimental conditions known in the art. Preferably this reaction is conducted in the presence of N-bromosuccinimide, N-iodosuccinimide, N-chlorosuccinimide, bromine, iodine, hydrobromic acid/hydrogen peroxide, in a suitable solvent, such as acetonitrile, N,N-dimethylformamide, dioxane, dimethylsulfoxide, acetic acid or water, at a temperature ranging from about room temperature to reflux and for a period of time varying from about 1 h to about 96 h.

According to step b), a compound of formula (IX) can be obtained by a two-steps reaction sequence from a compound of formula (X) in a variety of ways and experimental conditions known in the art. First step is preferably conducted in the presence of sodium nitrite/hydrochloric acid or tert-butylnitrile in a suitable solvent, such as tetrahydrofuran, dimethoxyethane, dimethylsulfoxide, acetic acid or water, at a temperature ranging from about −20° C. to room temperature and for a period of time varying from 10 min to about 24 h. Second step is preferably carried out in the presence of sodium, copper or potassium cyanide, often in the presence of an additive such as copper or potassium chloride, in a suitable solvent, such as tetrahydrofuran, dimethoxyethane, dimethylsulfoxide, acetic acid, toluene or water, at a temperature ranging from about −20° C. to reflux and for a period of time ranging from about 10 min to about 96 h.

According to step c), the hydrolysis of a compound of formula (IX) to a give a compound of formula (VIII) can be carried out in a variety of ways, according to conventional methods for transforming a cyano group to amide. Preferably this reaction is carried out in a suitable solvent such as, for instance, methanol, ethanol, butanol, 1,4-dioxane, toluene, water, or a mixture thereof, in the presence of a suitable acid or base, such as, for instance, sulfuric acid, methanesulfonic acid, hydrochloric acid, trifluoroacetic acid, sodium hydroxide, sodium carbonate, or a suitable reagent such as hydrogen peroxide, sodium perborate or indium(II) salts in the presence of acetaldoxime. Typically, the reaction is carried out at a temperature ranging from room temperature to reflux and for a time varying from about 1 h to about 96 h.

According to step d), a compound of formula (VIII) can be transformed into a compound of formula (VII) according to conventional methods. Preferably the reaction is carried out in the presence of water by treatment with a base such as potassium or sodium carbonate, potassium or sodium hydroxide, in a suitable solvent such as, for instance, methanol or ethanol, at a temperature ranging from room temperature to reflux, for a time ranging from about 30 min to about 96 h. Alternatively this reaction can be conducted in the presence of sodium nitrite/acetic acid, sulfuric acid, phosphoric acid, at a temperature ranging from room temperature to reflux and for a time varying from about 1 h to about 96 h.

According to step e), the halogenation of 4-fluoro-2-methyl-benzoic acid (XII) into a compound of formula (VII) can be carried out in a variety of ways, according to conventional methods for halogenation reactions. Preferably, this reaction is carried out with tetrabutylammonium bromide and/or iodine in the presence of phenyliodine(III) bis(trifluoracetate) or phenyliodo(III) diacetate as halogen source in a suitable solvent such as, for instance, N,N-dimethylformamide or dichloroethane, at a temperature ranging from room temperature to reflux and for a time varying from about 1 h to about 48 h. The catalyst is usually a metal, most often a palladium derivative such as, for instance, palladium(II) chloride or palladium(II) acetate.

According to step f), a compound of formula (VII) can be transformed into a compound of formula (VI) according to conventional methods. Preferably the reaction is carried out in the presence of hydrochloric acid, sulfuric acid or acetic acid by using as a solvent methanol, ethanol, water, or a mixture thereof, at a temperature ranging from room temperature to reflux and for a time varying from about 1 h to about 96 h. Alternatively, this reaction can be conducted with alkyl iodide, bromide or toluensulfonate in the presence of a suitable base, such as sodium or potassium carbonate, and sodium, lithium or potassium hydroxide, at a temperature ranging from room temperature to reflux and for a time varying from about 1 h to about 96 h.

According to step g), the transformation of a compound of formula (VI) into a compound of formula (V) can be carried out in a variety of ways, according to conventional methods for cyanation reactions. Preferably, this reaction is carried out in the presence of copper(I) cyanide or potassium hexacyanoferrate(II) as cyano source in a suitable solvent such as, for instance, methanol, ethanol, tetrahydrofuran, 1,4-dioxane, toluene, xylene, N-methyl-2-pyrrolidone, N,N-dimethylformamide, N,N-dimethylacetamide or a mixture thereof, at a temperature ranging from room temperature to reflux and for a time varying from about 1 h to about 96 h. If a catalyst is required, it is usually a metal, most often a palladium derivative such as, for instance, tetrakis(triphenylphosphine)palladium(0), palladium(II) chloride or palladium(II) acetate in the presence of a suitable base such as, for instance, sodium, potassium or cesium carbonate or cesium fluoride.

According to step h), a compound of formula (IV) can be obtained by a two-steps reaction sequence from a compound of formula (V) in the presence of a compound of formula (XIII) in a variety of ways and experimental conditions known in the art. First step is preferably conducted in the presence of N-bromosuccinimide with a radical initiator such as benzoyl peroxide or azobisisobutyronitrile in a suitable solvent, such as carbon tetrachloride, chloroform, dichloromethane or methyl pivalate, at a temperature ranging from about room temperature to reflux and for a period of time varying from 10 min to about 24 h. Second step can be conducted both under basic or acidic conditions, such as in the presence of sodium or potassium carbonate, 1,8-diazabicyclo[5.4.0]undec-7-ene, triethylamine, diisopropylethylamine, pyridine or acetic acid, hydrochloric acid, in a suitable solvent, such as tetrahydrofuran, dimethoxyethane, 1,4-dioxane or toluene, at a temperature ranging from room temperature to reflux and for a period of time varying from 1 h to about 96 h.

According to step c'), the hydrolysis of a compound of formula (IV) to give either a compound of formula (I) or a compound of formula (III), can be carried out in a variety of ways and experimental conditions. Preferably it is carried out in a way analogous to that reported for step c).

According to step i), when, in a compound of formula (III), X is a nitrogen protective group such as ter-butoxycarbonyl, 4-methoxybenzyl, 2,4-dimethoxybenzyl and triphenylmethyl protective groups, either a compound of formula (I) or a compound of formula (II) can be obtained by removing these protective groups under acidic conditions, preferably in the presence of an inorganic or organic acid such as hydrochloric, trifluoroacetic or methanesulphonic acid, boron tribromide or aluminium trichloride, in a suitable solvent, such as dichloromethane, dichloroethane, dioxane or a lower alcohol, such as methanol or ethanol, at a temperature ranging from room temperature to reflux. When, in a compound of formula (III), X is a nitrogen protective group such as benzyloxycarbonyl and the like, either a compound of formula (I) or a compound of formula (II) can be obtained by removing these protective groups under reducing conditions, such as, for instance, in the presence of hydrogen and a hydrogenation catalyst in a suitable solvent, such as ethanol, methanol, ethyl acetate, or a mixture thereof. The catalyst is usually a metal, most often a palladium derivative such as, for instance, palladium on carbon, palladium hydroxide or palladium black. When, in a compound of formula (III), X is a nitrogen protective group such as methoxycarbonyl, ethoxycarbonyl, 9-fluorenyl-methoxycarbonyl and the like, either a compound of formula (I) or a compound of formula (II) can be obtained by removing these protective groups under basic conditions such as, for instance, sodium, potassium or cesium carbonate, sodium, potassium or barium hydroxide, hydrazine, piperidine, morpholine or the like, in a suitable solvent, such as methanol, ethanol, water, N,N-dimethylformamide, N,N-dimethylacetamide or the like, at a temperature ranging from room temperature to reflux.

According to step l), the reductive alkylation of a compound of formula (II), in the presence of a compound of formula (XIV), to give a compound of formula (I), can be conducted in a variety of ways, according to conventional methods for carrying out reductive amination. Preferably, this reaction is carried out in a suitable solvent such as, for instance, methanol, N,N-dimethylformamide, dichloromethane, tetrahydrofuran, benzene, toluene, or a mixture thereof, in the presence of a suitable reducing agent such as, for instance, sodium borohydride, tetraalkylammonium borohydride, sodium cyano borohydride, sodium triacetoxyborohydride, tetramethylammonium triacetoxy borohydride and in the presence of an acid or basic catalyst, such as, for instance, acetic acid, trifluoroacetic acid, zinc chloride, zinc bromide, tin(V) chloride, titanium(IV) chloride, boron trifluoride or triethylamine, diisopropylethylamine or pyridine, at a temperature ranging from about 0° C. to reflux and for a time varying from about 1 h to about 96 h.

According to step m), a compound of formula (XVI) can be obtained from furan-2-carbaldehyde (XV) through reductive amination in the presence of a compound of formula (XIII). Preferably, this reaction is carried out in a suitable solvent such as, for instance, methanol, N,N-dimethylformamide, dichloromethane, tetrahydrofuran, benzene, toluene, or a mixture thereof, in the presence of a suitable reducing agent such as, for instance, sodium borohydride, tetraalkylammonium borohydride, sodium cyano borohydride, sodium triacetoxyborohydride or tetramethylammonium triacetoxy borohydride, and in the presence of an acid or basic catalyst, such as, for instance, acetic acid, trifluoroacetic acid, zinc chloride, zinc bromide, tin(IV) chloride, titanium(IV) chloride, boron trifluoride or triethylamine, diisopropylethylamine or pyridine, at a temperature ranging from about 0° C. to reflux and for a time varying from about 1 h to about 96 h.

According to step n), the Diels-Alder reaction, performed on a compound of formula (XVI) to give a compound of formula (XVII), can be conducted in a variety of ways, according to conventional methods for carrying out these reactions. Preferably, this reaction is carried out in a suitable solvent such as, for instance, tetrahydrofuran, benzene, toluene or o-xylene, in the presence of maleic anhydride at a temperature ranging from about room temperature to reflux and for a time varying from about 1 h to about 96 h.

According to step o), the transformation of a compound of formula (XVII) into either a compound of formula (XVIII) or a compound of formula (XIX), can be carried out in a variety of ways, according to conventional methods. Preferably, this reaction is carried out in a suitable solvent such as, for instance, tetrahydrofuran, toluene or water, in the presence of hydrochloric acid, p-toluenesulfonic acid or phosphoric acid, at a temperature ranging from about room temperature to reflux and for a time varying from about 1 h to about 24 h.

According to step p), a compound of formula (XVIII) can be reacted either to deliver a compound of formula (I) or a compound of formula (XX) in a variety of ways and experimental conditions, which are widely known in the art of condensation reactions. Preferably a compound of formula (XVIII) is reacted with ammonia or ammonia source such as ammonium salts, in the presence of an activating agent such as carbonyldiimidazole, benzotriazol-1-yloxy) tris(dimethylamino)phosphonium hexafluorophosphate, 2-(1H-benzotriazol-1-yl)-1,1,3,3-tetramethyluronium tetrafluoroborate), (O-(7-azabenzotriazol-1-yl)-N,N,N',N'-tetramethyluronium hexafluorophosphate, dicyclohexyl carbodiimide, diisopropyl carbodimide, 1-ethyl-3-(3'-dimethylamino) carbodiimide hydrochloric acid salt, optionally in the presence of hydroxybenzotriazole. Preferably, this reaction is carried out in a suitable solvent such as, for instance, N,N-dimethylformamide. N,N-dimethylacetamide, tetrahydrofuran, dichloromethane or 1,4-dioxane, and in the presence of a proton scavenger such as, for example, pyridine, triethylamine or diisopropylethylamine, at a temperature ranging from room temperature to reflux, for a time ranging from about 30 min to about 96 h.

According to step l'), the deprotection of a compound of formula (XX) to give a compound of formula (XXI), can be carried out in a variety of ways and experimental conditions. Preferably it is carried out in a way analogous to that reported for step i).

According to step l') the reductive alkylation of a compound of formula (XXI), in the presence of a compound of formula (XIV), to give a compound of formula (I), can be carried out in a variety of ways and experimental conditions. Preferably it is carried out in a way analogous to that reported for step l).

According to step q), the protection of compound of formula (XIX) to give a compound of formula (XVIII), where X is a suitable nitrogen protective group, may be carried out in a variety of ways and experimental conditions. Preferably, when the protective group is tert-butoxycarbonyl, the reaction may be carried out in the presence of di-tert-butyl dicarbonate in a variety of solvents such as methanol, ethanol, acetonitrile, tetrahydrofuran or dichloromethane, in the presence of a base, such as pyridine, N,N-dimethylaminopyridine, triethylamine, diisopropylethylamine, sodium or potassium carbonate, at a temperature ranging from room temperature to reflux and for a time varying from about 1 h to about 96 h.

According to the conversion 1 (Cv1), the reductive alkylation of a compound of formula (I) to give another compound of formula (I) may be carried out in a variety of ways and experimental conditions. Preferably, it is carried out in a way analogous to that reported for step l).

Substituted isoindolinone derivatives can be prepared using standard procedures in organic synthesis as reported, for instance, in Smith, Michael—March's Advanced Organic Chemistry: reactions mechanisms and structure—$6^{th}$ Edition, Michael B. Smith and Jerry March, John Wiley & Sons Inc., New York (N.Y.), 2007. It is known to the skilled person that transformation of a chemical function into another may require that one or more reactive centers in the compound containing this function have to be protected in order to avoid undesired side reactions. Protection of such reactive centers, and subsequent deprotection at the end of the synthetic transformations, can be accomplished following standard procedures described, for instance, in: Green, Theodora W. and Wuts, Peter G. M.—Protective Groups in Organic Synthesis, Third Edition, John Wiley & Sons Inc., New York (N.Y.), 1999.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques. Jean; Collet, Andre: Wien, Samuel H.—Enantiomers, Racemates, and Resolutions, John Wiley & Sons Inc., New York (N.Y.), 1981.

A compound of formula (I) can also be transformed into a pharmaceutically acceptable salt according to standard procedures that are known to those skilled in the art. Alternatively, a compound of formula (I) that is obtained as a salt can be transformed into the free base or the free acid according to standard procedures that are known to the skilled person.

The starting materials of the process of the present invention, i.e. 4-fluoro-2-methyl-phenylamine (XI), 4-fluoro-2-methyl-benzoic acid (XII), furan-2-carbaldehyde (XV) and compounds of formula (XIII) and (XIV) are either commercially available or can be prepared by using well-known methods.

Pharmacology

PARP-1 is a DNA damage-induced polymerase that catalyzes the cleavage of NAD+ into nicotinamide and ADP-ribose and then uses the latter to synthesize branched nucleic-acid like poly(ADP-ribose) polymers. In vivo, the most abundantly poly (ADP-ribosylated) protein is PARP-1 itself, followed by histones. PARP-1 is responsible for 90% of this DNA damage-induced activity while the remaining 10% is due to PARP-2.

Biochemical Assay

Affinity evaluation of the tested compounds and their selectivity with respect to the different PARP isoforms of interest was assessed in a displacement assay.

The identification of compounds capable of binding several PARP proteins is carried out through a screening method including the steps of
a) providing a reaction mixture containing:
the PARP protein isoform under investigation,
a compound of formula (IP):

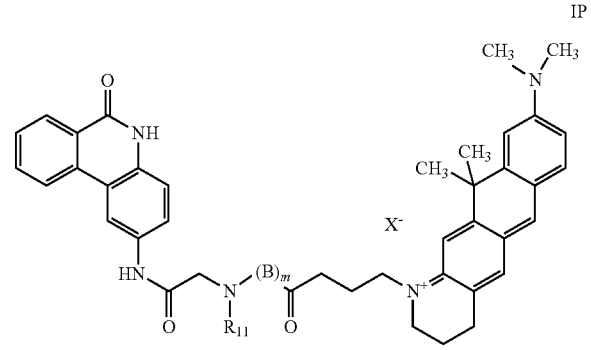

IP wherein $R_{11}$ is hydrogen or a methyl group. B is $(CH_2)_n$—NH group wherein n is 2 to 6; m is 0 or 1 and $X^-$ is a counterion, and serial dilutions of the test compound:
b) comparing the polarization signal generated in the absence of the test compound with the one generated in the presence of different concentrations of the test compound, and
c) evaluating the ability of the test compound to displace the compound of formula (IP) as defined above indicated from a decreased fluorescence polarization level.

Preferably, for the screening method above cited, both the PARP protein and the 5H-phenanthridin-6-one-derived probe of formula (IP) are pre-mixed, or the PARP protein and the test compound are pre-mixed. In a further preferred screening method, the PARP proteins are PARP-1. PARP-2 and PARP-3. The term "PARP protein" encompasses full-length native proteins as well as fragments thereof. More preferably, $R_{11}$ is hydrogen or methyl, m is 0 or 1; when m is 1, n is 3 or 6, $X^-$ is trifluoroacetate. The 5H-phenanthridin-6-one-derived probe (IP) was selected for its capability of binding to the PARP proteins, both encompassing full-length native proteins and fragments thereof.

The polarization signal can be measured, e.g., by a plate reader such as the Saphire2 (Tecan). Data analysis was performed, e.g., by using the Dynafit software. Displacement data were also fitted, e.g., by using Excel spreadsheet (Microsoft Inc. Seattle, USA) to a four parameter logistic model (4PL), or Hill-Slope model. The assay was used to test compounds of the present invention. The displacement ability of the test compounds of formula (I) is in correlation with the compounds affinity for the NAD pocket of the enzyme. Specific probes of formula (IP) used in the assay are:

P1. 9-Dimethylamino-11,11-dimethyl-1-(3-{methyl-[(6-oxo-5,6-dihydro-phenanthridin-2-ylcarbamoyl)-methyl]-carbamoyl}-propyl)-2,3,4,11-tetrahydro-naphtho[2,3-g]quinolinium trifluoroacetate;

P2. 9-Dimethylamino-11,11-dimethyl-1-[3-(3-{[(6-oxo-5,6-dihydro-phenanthridin-2-ylcarbamoyl)-methyl]-amino}-propylcarbamoyl)-propyl]-2,3,4,11-tetrahydro-naphtho[2,3-g]quinolinium trifluoroacetate;

P3. 9-Dimethylamino-11,11-dimethyl-1-[3-(6-{[(6-oxo-5,6-dihydro-phenanthridin-2-ylcarbamoyl)-methyl]-amino}-hexylcarbamoyl)-propyl]-2,3,4,11-tetrahydro-naphtho[2,3-g]quinolinium trifluoroacetate.

A compound of formula (IP) as defined above can be prepared as described in WO 2010/133647.

The assay is based on the use of a probe of formula (IP) that binds to the NAD binding pocket and takes advantage of the significant change in the polarization signal observed upon binding of the probe to PARP-1, -2 and -3. The ability of the probe of formula (IP) to bind full-length PARP-1, -2 and -3 has been previously reported (WO 2010/133647). The assay has been validated as described in WO 2010/133647.

Affinity binding constants (Kd) and $DC_{50}$s (the compound concentration at which the polarization signal is diminished by 50% compared to untreated controls) of the test compounds can be determined as explained in WO 20101133647. The assay, by using either probe P1 or probe P3, was used to evaluate the biochemical potency of compounds of formula (I) as reported in Table 1.

TABLE 1

| Compound | PARP-1 (DC$_{50}$ μM) | PARP-1 (Kd μM) | PARP-2 (DC$_{50}$ μM) | PARP-2 (Kd μM) | PARP-3 (DC$_{50}$ μM) | PARP-3 (Kd μM) |
|---|---|---|---|---|---|---|
| (2) | <0.25† | <0.03† | 0.34 | 0.18 | — | — |
| (3) | <0.25 | <0.03 | 7.1 | 5.8 | — | — |
| (4) | 0.39 | — | 1.92 | — | — | — |
| (5) | 0.33 | — | 1.64 | — | — | — |
| (6) | <0.25 | 0.04 | 7.44 | 5.87 | — | — |
| (7) | <0.25 | 0.06 | 0.76 | 0.42 | — | — |
| (8) | <0.25 | 0.05 | >10 | — | — | — |
| (9) | <0.25 | <0.03 | 4.94 | 1.44 | — | — |
| (10) | <0.25 | 0.07 | 8.4 | 6.8 | — | — |
| (11) | <0.25 | <0.01*† | 2.53 | 1.4 | 2.06 | — |
| (12) | <0.25 | <0.03 | 3.37 | 1.7 | — | — |
| (13) | <0.25 | <0.03 | 5.08 | — | — | — |
| (14) | <0.25 | <0.03 | 1.25 | 0.58 | — | — |
| (15) | <0.25 | 0.04 | >10 | — | 0.9 | — |
| (16) | <0.25 | <0.03 | 2.88 | 0.98 | — | — |
| (17) | <0.25 | <0.03 | 0.63 | 0.29 | — | — |
| (19) | <0.25 | <0.03 | 2.76 | 1.39 | — | — |
| (20) | <0.25 | <0.03 | 0.58 | 0.19 | — | — |
| (21) | 0.28 | — | >10 | — | — | — |
| (22) | <0.25 | <0.03 | 2.12 | — | — | — |
| (23) | <0.25 | <0.03 | 2.00 | — | — | — |
| (24) | <0.25 | <0.03 | 0.83 | 044 | — | — |
| (25) | <0.25 | — | 5.57 | — | — | — |
| (26) | 3.33 | — | >10 | — | — | — |
| (27) | 1.05 | — | >10 | — | — | — |
| (28) | <0.25 | <0.03 | 1.81 | — | 5.48 | — |
| (29) | <0.25 | <0.01*† | 2.92 | — | 1.00 | — |
| (30) | <0.25 | — | >10 | — | 0.35 | — |
| (31) | <0.25 | — | >10 | — | — | — |
| (32) | <0.25 | 0.048 | 1.88 | 0.66 | — | — |

*Assay performed with compound P3 as the probe, In all other cases compound P1 was used as the probe.
†Assay sensitivity limits based on a fitting error < 50%.

From the above data, it is clear to a person skilled in the art that compounds of formula (I) of the present invention are highly potent as PARP-1 inhibitors and extremely selective versus PARP-2 and PARP-3 (compare PARP-1, PARP-2 and PARP-3 DC$_{50}$ and Kd values in Table 1 above).

Cellular Assays
PAR Assay

Cellular activity of PARP-1 inhibitors was assessed by measuring the inhibition of the hydrogen peroxide induced PAR formation in HeLa cells (ECACC). Cellular PAR levels were measured by immunocytochemistry, and quantified using an ArrayScan vTi instrument (Cellomics Thermo Scientific).

Studies were performed as follows: 6000 cells/well were seeded in 96 well plates (Perkin Elmer) in MEM/10% FCS and incubated for 24 h at 37° C., 5% carbon dioxide. Test compounds were then added at the required concentration for 30 min. DNA damage was then induced adding hydrogen peroxide at the concentration of 0.1 mM for 15 min. Concentration curves were prepared in MEM/10% FCS from compound stocks in DMSO, and final DMSO concentration was 0.002% (v/v). Duplicate wells for each concentration point were prepared with a typical highest compound concentration of 20 μM and serial dilution 1:3. Plates were dried and fixed adding cold methanol-acetone (70:30) solution for 15 min at room temperature, fixing solution was aspired and wells were air dried for 5 min and then dehydrated in PBS. Non-specific binding sites were blocked by incubating wells for 30 min in PBS containing 5% (w/v) FBS 0.05% tween20. Wells were then incubated for 1 h at room temperature in PBS containing anti PAR mouse monoclonal antibody (Anti-PAR. Mouse mAb 10H, Tulip Cat No 1020) diluted 1:200 in blocking solution. After 3 washes in PBS, wells incubated in PBS (w/v) 5% FBS 0.05% Tween20 containing 2 μg/mL Cy2-conjugated Goat anti mouse secondary antibody (Amersham Pharmacia Biotech cat. No PA 42002) (Absorption maximum 489 nm fluorescence maximum 506 nm) and 1 μg/mL DAPI (Absorption maximum 359 nm fluorescence maximum 461 nm) (4',6-diamidino-2-phenylindole dilactate) (Sigma cat. No D9564), a high-sensitivity dye for nucleic acid staining. After washing further 3 times in PBS, cellular PAR immunoreactivity was assessed using the ArrayScan vTi instrument, with a Zeiss 10×0.5 NA objective, and applying the Cytotoxicity. V3 algorithm (Cellomics/Thermo Fisher) with a XF100 filter. At least 10 fields, corresponding to at least 900 cells, were read for each well. IC$_{50}$ Values represent the compound concentration at which cellular PAR signal is diminished by 50% compared with untreated controls.

The following formula is used:

$$IC_{50} = Bottom + (Top - Bottom)/(1 + 10^{((Log\ EC_{50} - X))});$$

X is the logarithm of concentration, IC$_{50}$ is the response; IC$_{50}$ starts at bottom and goes to top with a sigmoid shape. Given the above assays, compounds of formula (I) of the present invention inhibited PAR formation with IC$_{50}$ values lower than 5 μM, as depicted in Table 2.

TABLE 2

| Compound | PAR assay (IC$_{50}$ μM) |
|---|---|
| (3) | 2.25 |
| (6) | 2.15 |
| (9) | 1.40 |
| (11) | 0.02 |
| (12) | 3.9 |
| (13) | 0.98 |
| (14) | 0.011 |

TABLE 2-continued

| Compound | PAR assay (IC$_{50}$ µM) |
|---|---|
| (15) | 0.1 |
| (16) | 0.02 |
| (17) | 1.51 |
| (19) | 0.33 |
| (20) | 0.83 |
| (21) | 0.60 |
| (22) | 0.40 |
| (23) | 0.40 |
| (24) | 0.11 |
| (25) | 0.20 |
| (28) | 0.56 |
| (29) | 0.5 |
| (31) | 0.2 |
| (32) | 0.17 |

Colony Forming Assay

MDA-MB-436 breast cancer BRCA-1 mutated cells were grown at the density of 600 cells/cm$^2$ in RPMI medium supplemented with 10% Fetal Bovine Serum. 24 h later different doses of compounds were added starting from 10 µM concentration in duplicates. Ten days later, cells were fixed and stained with crystal violet. Colonies were counted using Infrared Scanner (Odyssey Li-Cor). Anti proliferative IC$_{50}$ was calculated using Prism.

Pharmacokinetics

The pharmacokinetic profile and the oral bioavailability of the compounds have been investigated in the mouse (Balb, Nu/Nu, Harlan, Italy) in ad hoc pharmacokinetic studies. The compounds were formulated in 10% tween 80/dextrose for intravenous bolus administration while oral administrations were performed using the compounds formulated in 0.5% methylcellulose. A single administration at the dose of 10 mg/kg was given and three male animals for each route were used. All blood samples were taken from retro-orbital vein at 5 min, 30 min, 1 h, 3 h, 6 h, 24 h after intravenous administration and 15 min, 30 min, 1 h, 3 h, 6 h, 24 h after oral administration. Plasma samples were prepared by plasma proteins precipitation adding 200 µL of acetonitrile to 20 µL of plasma in a 96 well plate. After capping and vortex mixing, the plate was centrifuged for 15 min at 4000 rpm. The supernatant was considered as final extract and injected onto the LC-MS-MS system (UPLC system: Waters Acquity using BEH C18 50*2.1 mm 1.7 µm analytical column; MS instrument Waters TOD equipped with Electro-Spray source operating in positive ion mode). Lower limit of quantification is 5.0 ng/mL, upper limit of quantification is 5000 ng/mL. Non-compartmental method (linear trapezoidal rule and linear regression analysis of natural log-transformed plasma concentrations vs. time data) was used Absolute bioavailability (F) was calculated from the ratio of average oral to IV (intravenous) dose-normalized plasma AUC (area under curve) values.

The abbreviations used herein have the following meaning:

AUC (area under the plasma concentration vs. time curve up to the last detectable concentration)
Cl (plasma clearance)
Cmax (maximum plasma concentration)
T½ (terminal half life)
Vdss (volume of distribution at steady state)

Some representative compounds of formula (I) were evaluated for their pharmacokinetic parameters as reported in Table 3 as mean value.

TABLE 3

| Compound | Cl(IV bolus) mL/min/kg | Vdss (IV bolus) L/Kg | AUC (oral) µM · h | Cmax (oral) µM | T½ (oral) h | F on AUC % |
|---|---|---|---|---|---|---|
| (3) | 63.1 | 1.54 | 2.51 | 3.06 | 0.68 | 30 |
| (11) | 41.3 | 4.47 | 20.4 | 3.87 | 2.72 | 100 |
| (14) | 81.8 | 2.68 | 3.22 | 2.29 | 0.89 | 57 |
| (15) | 16.9 | 0.79 | 19.2 | 8.73 | 1.01 | 68 |
| (16) | 79.3 | 2.51 | 2.13 | 2.97 | 0.63 | 37 |

From the above, it is clear to the person skilled in the art that compounds of formula (I) possess good to excellent pharmacokinetics profiles and oral bioavailability.

In Vivo Efficacy Studies

Balb, athymic Nu/Nu male mice, from Harlan (Italy), were maintained in agreement with the European Communities Council Directive no. 86/609/EEC concerning the protection of animals used for experimental or other scientific purposes, in cages with paper filter cover, food and bedding sterilized and acidified water. Fragments of Capan-1 human pancreatic cancer tumors were implanted subcutaneously. Mice bearing a palpable tumor (100-200 mm$^3$) were selected and randomized into control and treated groups. Each group included seven animals. The treatment started one day after randomization. Compound of formula (I) was administered by oral route as a methocel suspension at the indicated doses and times. Tumor dimension was measured regularly by calipers during the experiments and tumor mass was calculated as described in Simeoni M. et al., Cancer Res 64, 1094-1101 (2004). The tumor growth inhibition (TGI, %) was calculated according to the equation: % TGI=100−(mean tumor weight of treated group/mean tumor weight of control group)*100.

Some representative compounds of formula (I) were evaluated for their anti-tumor activity as single agent on Capan-1 BRCA-2 mutated mouse model and results are reported in table 4. Toxicity was evaluated on the basis of body weight reduction (no body weight reduction observed out of 7 mice treated).

TABLE 4

| Compounds | Dose | Schedule | Max TGI (%) | Toxicity |
|---|---|---|---|---|
| (11) | 75 mg/kg | 1-8 daily | 42% | 0/7 |
| (15) | 75 mg/kg | 1-10 daily | 54% | 0/7 |

Representative compounds of formula (I) were evaluated for their anti-tumor activity on Capan-1 BRCA-2 mutated mouse model in combination with temozolomide. Compounds of formula (I) and temozolomide were both administered by oral route. Tumor growth was assessed by caliper. The two diameters were recorded and the tumor weight was calculated according to the following formula: length (mm)× width$^2$/2. The effect of the antitumor treatment was evaluated as the delay in the onset of an exponential growth of the tumor (see for references Anticancer drugs 7:437-60, 1996). This delay (T-C value) was defined as the difference of time (in days) required for the treatment group (T) and the control group (C) tumors to reach a predetermined size (1 g). Toxicity was evaluated on the basis of body weight reduction and animal survival rate. The T-C observed when Compounds of formula (I) were combined with temozolomide was superior to the one expected by the simple addition of T-C obtained by the single treatments, thus indicating strong synergism.

Therefore, the present invention provides compounds of formula (I) useful in therapy.

Compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 1 to about 1000 mg per dose, from 1 to 5 times daily. The compounds of the invention can be administered in a variety of dosage forms. e.g., orally, in the form of tablets, capsules, sugar or film coated tablets, liquid solutions or suspensions; rectally in the form of suppositories; parenterally, e.g., intramuscularly, or through intravenous and/or intrathecal and/or intraspinal injection or infusion.

As stated above, the present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose, saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, such as propylene glycol, and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:
amu (atomic mass unit)
calcd. (calculated)
μM (micromolar)
μL (microliter)
μm (micrometer)
mol (moles)
mM (millimolar)
mmol (millimoles)
nm (nanometers)
g (grams)
mg (milligrams)
ng (nanograms)
h (hour/s)
min (minutes)
$DC_{50}$ (the half maximal Displacement Concentration)
$IC_{50}$ (the half maximal Inhibitory Concentration)
PAR (poly (ADP-ribose))
MEM (Minimal Essential Medium)
FCS (Fetal Calf Serum)
FBS (Fetal Bovine Serum)
PBS (Phosphate Buffered Saline)
LC-MS (Liquid Chromatography-Mass Spectrometry)
HPLC (High Performance Liquid Chromatography)
TLC (Thin Layer Chromatography)
MHz (megahertz)
Hz (Hertz)
DMSO-$d_6$ (deuterated dimethylsulfoxide)
$CDCl_3$ (deuterated chloroform)
ESI (electrospray ionization)

With the aim at better illustrating the present invention, without posing any limitation to it, the following examples are now given.

As used herein the symbols and conventions used in the processes, schemes and examples are consistent with those used in the contemporary scientific literature, for example, the *Journal of the American Chemical Society or the Journal of Biological Chemistry*.

Unless otherwise noted, all materials were obtained from commercial suppliers, of the best grade and used without further purification. Anhydrous solvent such as N,N-dimethylformamide, tetrahydrofuran, dichloromethane and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60 Å). HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid-acetonitrile 95:5), and mobile phase B was water-acetonitrile (5:95). Gradient from 10 to 90% B in 8 min, hold 90% B 2 min. UV detection at 220 nm and 254 nm. Flow rate 1 mL/min. Injection volume 10 μL. Full scan, mass range from 100 to 800 amu. Capillary voltage was 2.5 KV; source temperature was 120° C.; cone was 10 V. Retention times (HPLC r.t.) are given in min at 220 nm or at 254 nm. Mass are given as m/z ratio.

When necessary, compounds were purified by preparative HPLC on a Waters Symmetry C18 (19×50 mm, 5 μm)

column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Mobile phase A was water-0.01% trifluoroacetic acid, and mobile phase B was acetonitrile. Gradient from 10 to 90% B in 8 min, hold 90% B 2 min. Flow rate 20 mL/min. In alternative, mobile phase A was water-0.1% ammonium hydroxide, and mobile phase B was acetonitrile. Gradient from 10 to 100% B in 8 min, hold 100% B 2 min. Flow rate 20 mL/min.

$^1$H-NMR spectra were performed in DMSO-$d_6$ or CDCl$_3$ on a Varian Inova 400 operating at 400.5 MHz and on a Varian Mercury 300 operating at 300.0 MHz. $^{13}$C NMR spectra were performed in DMSO-A at 75.0 MHz.

Residual solvent signal was used as reference (δ=2.50 or 7.27 ppm). Chemical shifts (δ) are reported in parts per million (ppm) and coupling constants (J) in Hz. The following abbreviations are used for multiplicities; s=singlet; br. s.=broad signal; d=doublet; t=triplet; m=multiplet; dd=doublet of doublets.

ESI(+) high-resolution mass spectra (HRMS) were obtained on a Q-Tof Ultima (Waters, Manchester, UK) directly connected with a 1100 micro-HPLC system (Agilent, Palo Alto, US) as previously described (Colombo, M., Sirtori, F. R., and Rizzo. V. (2004) A fully automated method for accurate mass determination using high-performance liquid chromatography with a quadrupole/orthogonal acceleration time-of-flight mass spectrometer. Rapid Commun. Mass Spectrom, 18, 511-517).

Example 1

Step a

2-Bromo-4-fluoro-6-methyl-phenylamine (X) [Hal=Br]

A solution of N-bromosuccinimide (18.7 g, 0.105 mol) in 70 mL of N,N-dimethylformamide was added dropwise to a solution of 4-fluoro-2-methyl-phenylamine (XI) (12.5 g, 0.1 mol) in 70 mL of the same solvent at 20° C. The reaction mixture was stirred overnight. The dark solution was poured into a mixture of water (1000 mL), brine (50 mL) and ethyl acetate (300 mL). The mixture was transferred into a separatory funnel, shaken and separated. The aqueous phase was extracted with ethyl acetate (4×150 mL). The combined organic layers were washed with water (5×100 mL), brine (2×100 mL), dried over Na$_2$SO$_4$, filtered and concentrated. The product was purified by lash chromatography (eluent ethyl acetate:n-hexane=1:8). The pure fractions were combined and evaporated to give 14.9 g of product. The impure fractions were combined, concentrated, re-dissolved in diethyl ether (30 mL) and extracted with 5% hydrochloric acid (5×10 ml). The acidic phase was basified with aqueous potassium hydroxide and extracted with diethyl ether to provide further 0.8 g of the title compound. Total yield was 15.7 g (77%). $^1$H NMR (400.5 MHz, DMSO-$d_6$) δ ppm 2.16 (s, 3H), 4.83 (br. s, 2H), 6.91 (dd, $J_{H-F}$=9.3 Hz, $J_{H-H}$=2.9 Hz, 1H), 7.16 (dd, $J_{H-F}$=8.3 Hz, $J_{H-H}$=2.9 Hz, 1H).

Step b

2-Bromo-4-fluoro-6-methyl-benzonitrile (IX) [Hal=Br]

A solution of potassium cyanide (16.25 g, 0.25 mol) in 20 mL of water was added to a suspension of freshly prepared copper(I) chloride (9.5 g, 0.096 mol) in 40 mL of water. Toluene (30 mL) was then added and the mixture was chilled to 0° C. 2-Bromo-4-fluoro-6-methyl-phenylamine (X) (15.7 g, 0.077 mol) was added to a mixture of 16.5 ml of 36% aqueous hydrochloric acid and 40 mL of water. The resultant suspension was heated until a solution was formed. The solution was chilled to 2° C. and the amine hydrochloride precipitated. A solution of sodium nitrite (5.34 g, 0.078 mol) in 15 mL of water was slowly added, keeping the reaction mixture temperature below 5° C. Powdered sodium carbonate decahydrate was added in small portions to adjust the pH of the reaction mixture to about 7. The resultant solution of the diazonium salt was then slowly added to the previously prepared cyanocuprate reagent, again keeping the reaction temperature below 5° C. A bright red-orange precipitate formed. The reaction mixture was allowed to warm to 20° C. and kept at this temperature overnight. Then it was slowly heated to 70° C. for 1 h. The precipitate dissolved almost completely. The reaction mixture was allowed to cool to 20° C. and filtered. The organic phase was separated, and the aqueous phase was extracted with toluene (3×70 ml). The combined organic layers were washed with water (2×100 mL), brine (2×100 mL), dried over Na$_2$SO$_4$, filtered and concentrated. The crude nitrile (IX) (13.9 g, 84%) was used without further purification.

$^1$H NMR (400.5 MHz, DMSO-$d_6$) δ ppm 2.52 (s, 3H), 7.44 (dd, $J_{H-F}$=9.4 Hz, J=2.1 Hz, 1H), 7.73 (dd, $J_{H-F}$=8.2 Hz, $J_{H-H}$=2.1 Hz, 1H).

$^{13}$C NMR (75.0 MHz, DMSO-$d_6$) δ 115.8, 112.7 (d, $J_{C-F}$=3 Hz), 117.0 (d, $J_{C-F}$=23 Hz), 118.4 (d, $J_{C-F}$=27 Hz), 126.1 (d, $J_{C-F}$=11 Hz), 147.8 (d, $J_{C-F}$=11 Hz), 163.5 (d, $J_{C-F}$=257 Hz).

Step c

2-Bromo-4-fluoro-6-methyl-benzamide (VIII) [Hal=Br]

2-Bromo-4-fluoro-6-methyl-benzonitrile (IX) (0.428 g, 2 mmol) was heated in 70% aqueous sulfuric acid (2 mL) overnight at 150° C. The reaction mixture was poured into ice and extracted with ethyl acetate (4×2 mL). The organic phase was washed with water (4×2 mL), brine (2×2 mL), dried over Na$_2$SO$_4$, filtered and concentrated to give 300 mg of crude 2-bromo-4-fluoro-6-methyl-benzamide (VIII). Pure sample was obtained by recrystallization from benzene.

$^1$H NMR (400.5 MHz, DMSO-$d_6$) δ ppm 3.31 (s, 3H), 7.17 (dd, $J_{H-F}$=9.8 Hz, $J_{H-H}$=2.2 Hz, 1H), 7.41 (dd, $J_{H-F}$=8.6 Hz, $J_{H-H}$=2.2 Hz, 1H), 7.89 (br. s, 1H), 7.65 (br. s, 1H).

Step d

2-Bromo-4-fluoro-6-methyl-benzoic acid (VII) [Hal=Br]

2-Bromo-4-fluoro-6-methyl-benzamide (VIII) (0.9 g, 3.9 mmol) was dissolved in 75% aqueous sulfuric acid (4 mL) at 80° C. Sodium nitrite (0.5 g, 7.2 mmol) was carefully added in small portions during 1 h. The reaction mixture was chilled to 20° C. and cold water (15 ml) was added to the reaction mixture. The product was extracted with ethyl acetate (6×2 mL). The organic phase was washed with water (4×2 mL), brine (2×2 mL), dried over Na$_2$SO$_4$, filtered and concentrated to give 0.879 g (97%) of pure acid (VII).

$^1$H NMR (400.5 MHz, DMSO-$d_6$) δ ppm 2.31 (s, 1H), 7.22 (dd, $J_{H-F}$=9.6 Hz, $J_{H-H}$=2.2 Hz, 1H), 7.47 (dd, $J_{H-F}$=8.5 Hz, $J_{H-H}$=2.4 Hz, 1H), 13.7 (br. s, 1H).

$^{13}$C NMR (75.0 MHz, DMSO-d$_6$+CCl$_4$) δ ppm 19.5, 116.0 (d, J$_{C-F}$=22 Hz), 116.8 (d, J$_{C-F}$=24 Hz), 118.3 (d, J$_{C-F}$=10 Hz), 134.0 (d, J=3 Hz), 138.4 (d, J$_{C-F}$=8 Hz), 163.0 (d, J$_{C-F}$=250 Hz), 168.0.

Step f

2-Bromo-4-fluoro-6-methyl-benzoic acid methyl ester (VI) [Hal=Br; T=methyl]

A mixture of 2-bromo-4-fluoro-6-methyl-benzoic acid (VII) (1.94 g, 8.33 mmol), anhydrous potassium carbonate (1.72 g, 12.5 mmol), methyl iodide (2.36 g, 17 mmol) in N,N-dimethylformamide (15 mL) was vigorously stirred for 23 h at 20° C. The suspension was poured into 70 mL of water. A dense oil separated out. The product was extracted with ethyl acetate (4×25 mL). The organic phase was washed with water (5×20 mL), brine (2×20 mL), dried over Na$_2$SO$_4$, filtered and concentrated to give 2.07 g (quantitative yield) of 2-bromo-4-fluoro-6-methyl-benzoic acid methyl ester (VI).

$^1$H NMR (400.5 MHz, CDCl$_3$) δ ppm 2.35 (s, 3H), 3.96 (s, 3H), 6.91 (dd, J$_{H-F}$=9.0 Hz, J$_{H-H}$=2.2 Hz, 1H), 7.18 (dd, J$_{H-F}$=8.1 Hz, J$_{H-H}$=2.4 Hz, 1H).

Step q

2-Cyano-4-fluoro-6-methyl-benzoic acid methyl ester (V) [T=methyl]

A mixture of 2-bromo-4-fluoro-6-methyl-benzoic acid methyl ester (VI) (275 mg, 1.12 mmol), potassium hexacyanoferrate (II) (206 mg, 0.56 mmol), anhydrous sodium carbonate (237 mg, 2.24 mmol) and palladium(II) acetate (5 mg, 0.0224 mmol) in 3 mL of N-methylpyrrolidone was heated at 120° C. in a sealed tube under argon atmosphere overnight. The reaction mixture was diluted with dichloromethane and filtered through a pad of Celite. The organic phase was washed with water (13×6 mL), brine (2×6 mL), dried over Na$_2$SO$_4$, filtered and concentrated. Column chromatography (n-hexane/ethyl acetate:7/3) afforded 2-cyano-4-fluoro-6-methyl-benzoic acid methyl ester (76 mg, 35%).

$^1$H NMR (400.5 MHz, DMSO-d$_6$) δ ppm 2.42 (s, 3H), 3.93 (s, 3H), 7.65 (dd, J$_{HF}$=9.6, J$_{HH}$=2.6 Hz, 1H), 7.85 (dd, J$_{HF}$=8.3, 2.6 Hz, 1H).

Step h

6-Fluoro-2-(3-morpholin-4-yl-propyl)-3-oxa-2,3-dihydro-1H-isoindole-4-carbonitrile (IV) [n=3; R1=morpholin-4-yl; X=null, as m=0 and R2=null]

To a solution of 2-cyano-4-fluoro-6-methyl-benzoic acid methyl ester (V) (208 mg, 1.07 mmol) in methyl pivalate (2 mL), N-bromosuccinimide (310 mg, 1.74 mmol) and benzoylperoxide (20 mg, 0.097 mmol) were added. The reaction mixture was stirred at 85° C. under nitrogen atmosphere for 3 h. Crude was filtered on Gooch and washed with toluene. Volatiles were evaporated and the residue was dissolved in acetonitrile (3 mL). Triethylamine (0.41 mL, 2.9 mmol) and 3-morpholin-4-yl-propylamine (XIII) (140 mg, 0.97 mmol) were added and the reaction mixture was stirred at 90° C. for 3 h. Crude was diluted with dichloromethane and washed with 15% ammonium hydroxide. The organic phase was dried over Na$_2$SO$_4$, filtered and evaporated. Column chromatography (gradient from chloroform/methanol: 96/4 to chloroform/methanol: 94/6) afforded 6-fluoro-2-(3-morpholin-4-yl-propyl)-3-oxo-2,3-dihydro-1H-isoindole-4-carbonitrile (IV) (130 mg, 40% yield).

$^1$H NMR (400.5 MHz, CDCl$_3$) δ ppm 1.87 (quintet, J=7.1 Hz, 2H), 2.34-2.49 (m, 6H), 3.62-3.74 (m, 6H), 4.45 (s, 2H), 7.42 (dd, J$_{H-F}$=7.3 Hz, J$_{H-H}$=2.0 Hz, 1H), 7.47 (dd, J$_{H-F}$=8.3 Hz, J$_{H-H}$=2.0 Hz, 1H).

Step c'

6-Fluoro-2-(3-morpholin-4-yl-propyl)-3-oxo-2,3-dihydro-1H-isoindole-4-carboxylic acid amide (I), cpd 23 [R=F; n=3; R1=morpholin-4-yl; m=0; R2=null]

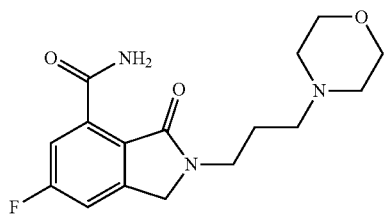 [SMILES: NC(=O)c1cc(F)cc2c1C(=O)N(CCCN1CCOCC1)C2]

A solution of 6-fluoro-2(3-morpholin-4-yl-propyl)-3-oxo-2,3-dihydro-1H-isoindole-4-carbonitrile (IV) (100 mg, 0.33 mmol) in 1.5 mL of 36% hydrochloric acid was heated at 50° C. for 10 h. All volatile materials were evaporated and the residue was dissolved in 2 mL of cold water. The solution was neutralized with solid potassium carbonate. The solid precipitated was dissolved in dichloromethane and the organic phase was washed with saturated aqueous sodium carbonate (2×1 mL), brine (2×1 mL), dried over Na$_2$SO$_4$, filtered and concentrated to give 73 mg (73%) of 6-fluoro-23-morpholin-4-yl-propyl)-3-ox-2,3-dihydro-1H-isoindole-4-carboxylic acid amide (I).

$^1$H NMR (400.5 MHz, DMSO-d$_6$) δ ppm 1.79 (quintet, J=7.1 Hz, 2H), 2.28-2.35 (m, 6H), 3.47-3.52 (m, 4H), 3.59 (t, J=7.1 Hz, 2H), 4.58 (s, 2H), 7.68 (dd, J$_{HF}$=7.8, J$_{HH}$=2.6 Hz, 1H), 7.83 (br. s., 1H), 7.89 (dd, J$_{HF}$=10.9, J$_{HH}$=2.6 Hz, 1H), 10.81 (br. s., 1H).

HRMS (ESI+): calcd. for C$_{16}$H$_{21}$FN$_3$O$_3$[M+H]$^+$ 322.1562; found 322.1565.

Example 2

Step e

4-Fluoro-2-iodo-6-methyl-benzoic acid (Vii) [Hal=I]

A mixture of 4-fluoro-2-methyl-benzoic acid (XII) (20.00 g, 0.130 mol), iodobenzene diacetate (50.15 g, 0.156 mol), iodine (39.52 g, 0.156 mol) and palladium(II) acetate (1.46 g, 0.006 mol) in N,N-dimethylformamide (360 mL) was degassed by cycling vacuum and nitrogen three times and then was heated for 18 h at 100° C. internal temperature, under argon. The resultant dark mixture was cooled to room temperature, diluted with methyl-tert-butylether (200 mL) and treated with a solution of sodium metabisulfite (250 g) in water (500 mL) under efficient stirring. Then, this yellow colored mixture was acidified by slowly adding conc. hydrochloric acid (130 mL). The aqueous layer was separated and extracted twice with methyl-tert-butylether (ml100×2). The combined organic extracts were treated with a solution of sodium hydroxide pellets (80 g) in water (300 mL) under stirring. The organic layer containing only iodobenzene was discharged, while the aqueous layer was added with sodium chloride, cooled to ice temperature and brought to very low pH with conc. hydrochloric acid (130 mL). From this aqueous medium the product was extracted with methyl-tert-butylether (100 mL×3) and the combined extracts were dried over Na$_2$SO$_4$ and finally concentrated under reduced pressure affording 30.5 g (84%) of 4-fluoro-2-iodo-6-methyl-benzoic acid as brown solid. This raw material was used in the next step without purification.

$^1$H NMR (300.0 MHz, CDCl$_3$) δ ppm 2.46 (s, 3H), 6.96 (dd, J$_{HF}$=9.1, J$_{HH}$=2.6 Hz, 1H), 7.45 (dd, J$_{HF}$=7.9, 2.3 Hz, 1H).

Step f

4-Fluoro-2-iodo-6-methyl-benzoic acid methyl ester (VI) [Hal=1; T=methyl]

To a solution of 4-fluoro-2-iodo-6-methyl-benzoic acid (VII) (30.05 g, 0.109 mol) in N,N-dimethylformamide (300 mL) was added anhydrous potassium carbonate (22.0 g, 0.16 mol) under efficient magnetic stirring. After 15 min methyl p-toluensulfonate (30.7 g, 0.16 mol) was added. The brown suspension was stirred at room temperature for 2 h. Potassium acetate (12.4 g, 0.13 mol) was then added to destroy the unreacted methyl p-toluensulfonate and the mixture was stirred overnight. The thick reaction mixture was diluted with methyl-tert-butylether (100 mL) and washed with water (600 mL); the aqueous layer was separated and extracted twice with methyl-tert-butylether (70 mL×2). The combined organic extracts were washed with brine (50 mL), dried over Na$_2$SO$_4$ and concentrated under reduced pressure to a solid residue. This material was purified by chromatography (eluant r-hexane/ethyl acetate 9:1), affording 26.2 g (81%) of product as colorless oil.

$^1$H NMR (400.5 MHz, DMSO-d$_6$) δ ppm 2.27 (s, 3H), 3.86 (s, 3H), 7.25 (dd, J$_{HF}$=9.6, J$_{HF}$=2.4 Hz, 1H), 7.63 (dd. J$_{HF}$=8.2, J$_{HH}$=2.4 Hz, 1H).

Step q

2-Cyano-4-fluoro-6-methyl-benzoic acid methyl ester (V) [T=methyl]

A solution of 4-fluoro-2-iodo-6-methyl-benzoic acid methyl ester (VI) (26.02 g, 88.48 mmol) in 260 mL of N,N-dimethylformamide was treated with copper(I) cyanide (12.18 g; 0.136 mol) and stirred at 110° C. for 5 h. The dark colored mixture was allowed to cool to about 60° C., treated with 105 g of Celite 560 coarse (Fluka) under efficient stirring and diluted with ethyl acetate (250 mL). After cooling to room temperature, the mixture was slowly poured in 0.25N aqueous sodium hydroxide (500 mL) and then filtered. The reaction flask and the panel were washed with ethyl acetate (100 mL). The aqueous layer was separated and extracted twice with ethyl acetate (250 mL+100 mL). The combined organic extracts were washed with brine (200 mL), dried over Na$_2$SO$_4$ and concentrated under reduced pressure to give 22.00 g of raw product as yellow solid. This material was crystallized from n-hexane (40 mL): after cooling to room temperature the solid was collected by filtration and the mother liquors were concentrated under reduced pressure. The solid residue so obtained was crystallized from n-hexane (20 mL) yielding, after filtration of the solids, a second crop of product. The combined crops (14.15 g) were finally purified by chromatography eluting in gradient from n-hexane/methyl-tert-butylether 9:1 to n-hexane/ethyl acetate 9:1. After evaporation of the fractions 12.0 g (70%) of 2-cyano-4-fluoro-6-methyl-benzoic acid methyl ester (V) were obtained.

$^1$H NMR (400.5 MHz, DMSO-d$_6$) δ ppm 2.42 (s, 3H), 3.93 (s, 3H), 7.65 (dd, J$_{HF}$=9.6, J$_{HH}$=2.6 Hz, 1H), 7.85 (dd, J$_{HF}$=8.3, 2.6 Hz, 1H).

Step h 2-(1-Cyclohexyl-piperidin-4-yl)-6-fluoro-3-oxo-2,3-dihydro-1H-isoindole-4-carbonitrile (IV) [R=F; n=m=0; R1=piperidin-4-yl; R2=1-cyclohexyl]

To a solution of 2-cyano-4-fluoro-6-methyl-benzoic acid methyl ester (V) (208 mg, 1.07 mmol) in methyl pivalate (2 mL), N-bromosuccinimide (310 mg, 1.74 mmol) and benzoylperoxide (20 mg, 0.097 mmol) were added. The reaction mixture was stirred at 85° C. under nitrogen atmosphere for 3 h. Crude was filtered and washed with toluene. Volatiles were evaporated and the residue was dissolved in acetonitrile (3 mL). Potassium carbonate (670 mg, 4.85 mmol) and 1-cyclohexyl-piperidin-4-ylamine dihydrochloride monohydrate (XIII) (265 mg, 0.97 mmol) were added and the reaction mixture was stirred at 90° C. for 3 h. Crude was diluted with dichloromethane and washed with 15% ammonium hydroxide. The organic phase was dried over Na$_2$SO$_4$, filtered and evaporated. Column chromatography (dichloromethane/methanol/ammonia solution, 7N in methanol: 97211) afforded 2-(1-cyclohexyl-piperidin-4-yl)-6-fluoro-3-oxo-2,3-dihydro-1H-isoindole-4-carbonitrile (IV) (100 mg, 30%).

$^1$H NMR (400.5 MHz, DMSO-d$_6$) δ ppm 1.02-1.13 (m, 1H), 1.16-1.27 (m, 4H), 1.55-1.62 (m, 1H), 1.68-1.80 (br. s., 7H), 2.23-2.39 (m, 3H), 2.87-2.97 (m, 2H), 3.95 (br. s., 1H), 4.52 (s, 2H), 7.86 (dd, J$_{HF}$=8.3, J$_{HH}$=2.2 Hz, 1H), 7.98 (dd, J$_{HF}$=9.3, J$_{HH}$=2.2 Hz, 1H).

HRMS (ESI+): calcd. for C$_{20}$H$_{25}$FN$_3$O [M+H]$^+$ 342.1976; found 342.1988.

Step c'

2-(1-Cyclohexyl-piperidin-4-yl)-fluoro-3-oxo-2,3-dihydro-1H-isoindole-4-carboxylic acid amide (I), cpd 29 [R=F; n=m=0; R1=piperidin-4-yl; R2=1-cyclohexyl]

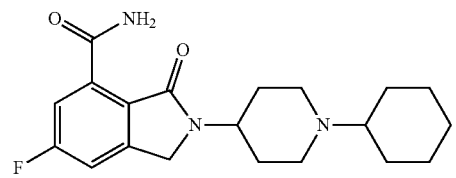 [SMILES: NC(=O)c1cc(F)cc2c1C(=O)N(C1CCN(C3CCCCC3)CC1)C2]

To a stirred solution of 2-(1-cyclohexyl-piperidin-4-yl)-6-fluoro-3-oxo-2,3-dihydro-1H-isoindole-4-carbonitrile (IV) (100 mg, 0.3 mmol) in acetic acid (5 mL), concentrated sulfuric acid (2.7 mL) was added dropwise during 30 min. The reaction was then warmed at 80° C. for 9 h, cooled at room temperature and poured into cold water (10 mL). The aqueous phase was then made basic by adding concentrated aqueous ammonia and extracted with dichloromethane (3×10 mL). The combined organic phases were washed with 2N aqueous sodium hydroxide (2×12 mL) and brine, dried over Na$_2$SO$_4$ and evaporated to dryness in vacuo. The title compound was obtained as a white solid (43 mg, 40%) after purification through column chromatography ((dichloromethane/methanol/ammonia solution, 7N in methanol: 97/2/1).

¹H NMR (400.5 MHz, DMSO-d₆) δ ppm 1.00-1.14 (m, 1H), 1.14-1.28 (m, 4H), 1.53-1.61 (m, 1H), 1.67-1.80 (m, 6H), 2.25-2.36 (m, 3H), 2.88-2.95 (m, 2H), 3.94-4.03 (m, 1H), 4.55 (s, 2H), 7.66 (dd, $J_{HF}$=7.7, $J_{HH}$ 2.6 Hz, 1H), 7.85 (br. s., 1H), 7.89 (dd, $J_{HF}$=10.9, $J_{HH}$=2.6 Hz, 1H), 10.78 (br. s., 1H).

HRMS (ESI+): calcd. for $C_{20}H_{27}FN_3O_2[M+H]^+$ 360.2082; found 360.2098.

Example 3

Step m

4-[(Furan-2-ylmethyl)-amino]-piperidine-1-carboxylic acid tert-butyl ester (XVI) [n=0; R1=piperidin-4-yl; X=tert-butoxycarbonyl]

To an equimolar solution of furan-2-carbaldehyde (XV) (250 mg, 2.6 mmol) and 4-amino-piperidine-1-carboxylic acid tert-butyl ester (XIII) (473 mg, 2.6 mmol) in dichloromethane (14 mL) 1M titanium(IV) chloride in dichloromethane (1.3 mL, 1.3 mmol) and triethylamine (0.32 mL, 2.6 mmol) were added. The reaction mixture was stirred under nitrogen atmosphere for 2 days. Then sodium cyanoborohydride (493 mg, 7.8 mmol) in methanol (7 mL) was added dropwise with stirring and the solution was allowed to stir overnight at room temperature, 35% sodium hydroxide was added and the product was extracted with ethyl acetate. The organic phase was separated, washed with brine, dried over Na₂SO₄ and evaporated to dryness in vacuo. The crude was purified by flash chromatography (dichloromethane/methanol 95:5) to give the title compound as a red oi (406 mg, 56%).

HRMS (ESI+): calcd. for $C_{12}H_{25}N_2O_3[M+H]^+$ 281.1860; found 281.1867.

Operating in an analogous way, but employing suitably substituted starting material (XIII), the following compounds were obtained:

Benzyl-furan-2-ylmethyl-amine (XVI)
HRMS (ESI+): calcd. for $C_{12}H_{14}NO [M+H]^+$ 188.1070; found 188.1075.

Furan-2-ylmethyl-phenethyl-amine (XVI)
HRMS (ESI+): calcd. for $C_{13}H_{16}NO [M+H]^+$ 202.1226; found 202.1230.

[2-(3,4-Dihydro-1H-isoquinolin-2-yl)-ethyl]-furan-2-ylmethyl-amine (XVI)
HRMS (ESI+): calcd. for $C_{16}H_{21}N_2O [M+H]^+$ 257.1648; found 257.1642.

Furan-2-ylmethyl-(2-piperidin-1-yl-ethyl)-amine (XVI)
HRMS (ESI+): calcd. for $C_{12}H_{21}N_2O [M+H]^+$ 209.1648; found 209.1650.

Furan-2-ylmethyl(2-morpholin-4-yl-ethyl)-amine (XVI)
HRMS (ESI+): calcd. for $C_{11}H_{19}N_2O_2 [M+H]^+$ 211.1441; found 211.1446.

Furan-2-ylmethyl-(3-morpholin-4-yl-propyl)-amine (XVI)
HRMS (ESI+): calcd. for $CH_{21}H_{21}N_2O_2 [M+H]^+$ 225.1598; found 225.1590.

[2-(3,4-Dihydro-2H-quinolin-1-yl)-ethyl]-furan-2-ylmethyl-amine (XVI)
HRMS (ESI+): calcd. for $C_{16}H_{21}N_2O [M+H]^+$ 257.1648; found 257.1652.

Furan-2-ylmethyl-(3-phenyl-propyl)-amine (XVI)
HRMS (ESI+): calcd. for $C_{14}H_{18}NO [M+H]^+$ 216.1383; found 216.1387.

Furan-2-ylmethyl-(2-pyridin-2-yl-ethyl)-amine (XVI)
HRMS (ESI+): calcd. for $C_{12}H_{15}N_2O [M+H]^+$ 203.1179; found 203.1181.

[3-(3,4-Dihydro-1H-isoquinolin-2-yl)-propyl]-furan-2-ylmethyl-amine (XVI)
HRMS (ESI+): calcd. for $C_{17}H_{23}N_2O [M+H]^+$ 271.1805; found 271.1799.

[3-(3,4-Dihydro-2H-quinolin-1-yl)-propyl]-furan-2-ylmethyl-amine (XVI)
HRMS (ESI+): calcd. for $C_{17}H_{23}N_2O [M+H]^+$ 271.1805; found 271.1811.

Furan-2-ylmethyl-[3-(4-methyl-piperazin-1-yl)-propyl]-amine (XVI)
HRMS (ESI+): calcd. for $C_{13}H_{24}N_3O [M+H]^+$ 238.1914; found 238.1912.

Furan-2-ylmethyl[3-(4-phenyl-piperazin-1-ylpropyl]-amine (XVI)
HRMS (ESI+): calcd. for $C_{18}H_{26}N_3O [M+H]^+$ 300.2070; found 300.2077.

Furan-2-ylmethyl-(3-piperidin-1-yl-propyl)-amine (XVI)
HRMS (ESI+): calcd. for $C_{13}H_{23}N_2O [M+H]^+$ 223.1805; found 223.1802.

(3-[1,4']Bipiperidinyl-1'-yl-propyl)-furan-2-ylmethyl-amine (XVI)
HRMS (ESI+): calcd. for $C_{18}H_{32}N_3O [M+H]^+$ 306.2540; found 306.2544.

[3-(2,6-Dimethyl-piperidin-1-yl)-propyl]-furan-2-ylmethyl-amine (XVI)
HRMS (ESI+): calcd. for $C_{15}H_{27}N_2O [M+H]^+$ 251.2118; found 251.2120.

Furan-2-ylmethyl-[1-(tetrahydro-pyran-4-yl)-piperidin-4-yl]-amine (XVI)
HRMS (ESI+): calcd. for $C_{15}H_{25}N_2O_2 [M+H]^+$ 265.1911; found 265.1919.

(1-Benzyl-piperidin-4-yl)-furan-2-ylmethyl-amine (XVI)
HRMS (ESI+): calcd. for $C_{17}H_{23}N_2O [M+H]^+$ 271.1805; found 271.1807.

[2-(1-Benzyl-piperidin-4-yl)-ethyl]furan-2-ylmethyl-amine (XVI)
HRMS (ESI+): calcd. for $C_{19}H_{27}N_2O [M+H]^+$ 299.2118; found 299.21222.

[3-(4-Benzyl-piperidin-1-yl)-propyl]-furan-2-ylmethyl-amine (XVI)
HRMS (ESI+): calcd. for $C_{20}H_{29}N_2O [M+H]^+$ 313.2274; found 313.2280.

(1-Cyclohexyl-piperidin-4-yl)-furan-2-ylmethyl-amine (XVI)

An equimolar solution of furan-2-carbaldehyde (XV) (1.3 g, 13.5 mmol) and 1-cyclohexyl-piperidin-4-ylamine (XIII) (2.46 g, 13.5 mmol) in toluene (140 mL) was heated to reflux for 8 h by employing a Dean-Stark apparatus. The reaction mixture was concentrated under vacuum and rinsed with ethanol (50 mL). Sodium triacetoxyborohydride (3.8 g, 17.93 mmol) was added and the mixture was left overnight at room temperature. Then it was basified with aqueous ammonia (8%) and the aqueous layer was separated and extracted with diethyl ether. The organic phase was dried over anhydrous sodium sulfate and concentrated under reduced pressure to give the title compound as a yellow oil employed in the following step without any further purification.

HRMS (ESI+): calcd. for $C_{16}H_{27}N_2O [M+H]^+$ 263.2118; found 263.2120.

Step n 3-(1-Tert-butoxycarbonyl-piperidin-4-yl)-4-oxo-10-oxa-3-aza-tricyclo[5.2.1.0*1,5*]dec-8-ene-6-carboxylic acid (XVII) [n=0; R1=piperidin-4-yl; X=tert-butoxycarbonyl]

To a solution of 4-[(furan-2-ylmethyl)-amino]-piperidine-1-carboxylic acid tert-butyl ester (XVI) (5.6 g, 21 mmol) in toluene (300 mL) maleic anhydride (2.1 g, 21 mmol) was added. The reaction mixture was refluxed for 6 h and stirred overnight at room temperature. The precipitate solid obtained was filtered, washed with diethyl ether and dried to give the desired compound (6.5 g, 82%) as a white solid.

$^1$H NMR (400.5 MHz, DMSO-d$_6$) δ ppm 1.40 (s, 9H), 1.40-1.63 (m, 4H), 2.45 (d, J=9.3 Hz, 1H), 2.75 (br. s., 2H), 2.76 (d, J=9.3 Hz, 1H), 3.59 (d, J=11.6 Hz, 1H), 3.88 (d, J=11.60 Hz, 1H), 3.90 (m, 1H), 3.96-4.06 (m, 2H), 4.95 (d, J=1.6 Hz, 1H), 6.42 (dd, J=5.6, 1.7 Hz, 1H), 6.55 (d, J=5.6 Hz, 1H), 12.03 (br. s., 1H).

HRMS (ESI+): calcd. for $C_{19}H_{27}N_2O_6$ [M+H]$^+$ 379.1864; found 379.1876.

Operating in an analogous way, but employing suitably substituted starting material (XVI) the following compounds were obtained:

3-Benzyl-4-oxo-10-oxa-3-aza-tricylo[5.2.1.0*1,5*]dec-8-ene-6-carboxylicacid (XVII)
HRMS (ESI+): calcd. for $C_{16}H_{16}NO_4$ [M+H]$^+$ 286.1074; found 286.1078.

4-Oxo-3-phenethyl-10-oxa-3-aza-tricyclo[5.2.1.0*1,5*]dec-8-ene-6-carboxylic acid (XVII)
HRMS (ESI+): calcd. for $C_{17}H_{23}N_2O_4$ [M+H]$^+$ 300.1230; found 300.1237.

3-[2-(3,4-Dihydro-1H-isoquinolin-2-yl)-ethyl]-4-oxo-10-oxa-3-aza-tricyclo[5.2.1.0*1,5*]dec-8-ene-6-carboxylic acid (XVII)
HRMS (ESI+): calcd. for $C_{20}H_{23}N_2O_4$ [M+H]$^+$ 355.1652; found 355.1657.

4-Oxo-3-(2-piperidin-1-yl-ethyl)-10-oxa-3-aza-tricyclo[5.2.1.0*1,5']dec-8-ene-6-carboxylic acid (XVII)
HRMS (ESI+): calcd. for $C_{16}H_2N_2O_4$ [M+H]$^+$ 307.1652; found 307.1660.

3-(2-Morpholin-4-yl-ethyl)-4-oxo-10-oxa-3-aza-tricyclo[5.2.1.0*1,5']dec-8-ene-6-carboxylic acid (XVII)
HRMS (ESI+): calcd. for $C_{15}H_{21}N_2O_5$ [M+H]$^+$ 309.1445; found 309.1446.

3-(3-Morpholin-4-yl-propyl)-4-oxo-1-oxa-3-aza-tricyclo[5.2.1.0*1,5*]dec-8-ene-6-carboxylicacid (XVII)
HRMS (ESI+): calcd. for $C_{16}H_{23}N_2O_4$ [M+H]$^+$ 323.1601; found 323.1609.

3-[2-(3,4-Dihydro-2H-quinolin-1-yl)-ethyl]-4-oxo-10-oxa-3-aza-tricyclo[5.2.1.0*1,5*]dec-8-ene-6-carboxylic acid (XVII)
HRMS (ESI+): calcd. for $C_{20}H_{23}N_2O_4$ [M+H]$^+$ 355.1652; found 355.1660.

4-Oxo-3-(3-phenyl-propyl)-1-oxa-3-aza-tricyclo[5.2.1.0*1,5*]dec-8-ene-6-carboxylic acid (XVII)
HRMS (ESI+): calcd. for $C_{18}H_{20}NO_4$ [M+H]$^+$ 314.1387; found 314.1392.

4-Oxo-3-(2-pyridin-2-yl-ethyl)-10-oxa-3-aza-tricyclo[5.2.1.0*1,5*]dec-8-ene-6-carboxylic acid (XVII)
HRMS (ESI+): calcd. for $C_{16}H_{18}N_2O$ [M+H]$^+$ 301.1183; found 301.1179.

3-[3-(3,4-Dihydro-1H-isoquinolin-2-yl)-propyl]-4-oxo-10-oxa-3-aza-tricyclo[5.2.1.0*1,5*]dec-ene-6-carboxylic acid (XVII)
HRMS (ESI+): calcd. for $C_{21}H_{25}N_2O_4$ [M+H]$^+$ 369.1809; found 369.1811.

3-[3-(3,4-Dihydro-2H-quinolin-1-yl)-propyl]-4-oxo-10-oxa-3-aza-tricyclo[5.2.1.0*1,5*]dec-8-ene-6-carboxylic acid (XVII)
HRMS (ESI+): calcd. for $C_{21}H_{25}N_2O_4$ [M+H]$^+$ 369.1809; found 369.1801.

3-[3-(4-Methyl-piperazin-1-yl)-propyl]-4-oxo-10-oxa-3-aza-tricyclo[5.2.1.0*1.5*]dec-8-ene-6-carboxylic acid (XVII)
HRMS (ESI+): calcd. for $C_{17}H_{26}N_3O_4$ [M+H]$^+$ 336.1918; found 336.1920.

4-Oxo-3-[3-(4-phenyl-piperazin-1-yl)-propyl]-10-oxa-3-aza-tricyclo[52.1.0*1,5*]dec-8-ene-6-carboxylic acid (XVII)
HRMS (ESI+): calcd. for $C_{22}H_{28}N_3O_4$ [M+H]$^+$ 398.2074; found 398.2079.

4-Oxo-3-(3-piperidin-1-yl-propyl)-10-oxa-3-aza-tricyclo[5.2.1.0*1,5*]dec-8-ene-6-carboxylic acid (XVII)
HRMS (ESI+): calcd. for $C_{17}H_{25}N_2O_4$ [M+H]$^+$ 321.1809; found 321.1812.

3-(3-[1,4']Bipiperidinyl-1'-yl-propyl)-4-oxo-10-oxa-3-aza-tricyclo[5.2.1.0*1,5*]dec-8-ene-6-carboxylic acid (XVII)
HRMS (ESI+): calcd. for $C_{22}H_{34}N_3O_4$ [M+H]$^+$ 4042544; found 404.2540.

3-[3-(2,6-Dimethyl-piperidin-1-yl)-propyl]-4-oxo-10-oxa-3-aza-tricyclo[5.2.1.0*1,5*]dec-8-ene-6-carboxylicacid (XVII)
HRMS (ESI+): calcd. for $C_{19}H_{29}N_2O_4$ [M+H]$^+$ 3492122; found 349.2119.

4-Oxo-3-[1-(tetrahydro-pyran-4-yl)-piperidin-4-yl]-10-oxa-3-aza-tricyclo[52.1.0*1,5]dec-8-ene-6-carboxylic acid (XVII)
HRMS (ESI+): calcd. for $C_{19}H_{27}N_2O$ [M+H]$^+$ 363.1914; found 363.1920.

3-(1-Benzyl-piperidin-4-yl)-4-oxo-10-oxa-3-aza-tricyclo[5.2.1.0*1,5*]dec-8-ene-6-carboxylicacid (XVII)
HRMS (ESI+): calcd. for $C_{21}H_{25}N_2O_4$ [M+H]$^+$ 369.1809; found 369.1799.

3-[2-(1-Benzyl-piperidin-4-yl)-ethyl]-4-oxo-10-oxa-3-aza-bicyclo[5.2.1.0*1,5*]dec-8-ene-6-carboxylic acid (XVII)
HRMS (ESI+): calcd. for $C_{23}H_{29}N_2O_4$ [M+H]$^+$ 397.2122; found 397.2127.

3-[3-(4-Benzyl-piperidin-1-yl)-propyl]-4-oxo-10-oxa-3-aza-tricyclo[5.2.1.0*1,5*]dec-8-ene-6-carboxylic acid (XVII)
HRMS (ESI+): calcd. for $C_{24}H_{31}N_2O_4$ [M+H]$^+$ 411.2278; found 411.2283.

3-(1-Cyclohexyl-piperidin-4-yl)-4-oxo-10-oxa-3-aza-tricyclo[5.2.1.0*1,5*]dec-8-ene-6-carboxylic acid (XVII)
$^1$H NMR (400.5 MHz, DMSO-d$_6$) δ ppm 11.98 (br.s., 1H), 6.58 (d, J=5.6 Hz, 1H), 6.44 (dd, J=5.6, 1.6 Hz, 1H), 4.97 (d, J 1.6 Hz, 1H), 4.00-4.11 (m, 1H), 3.96 (d, J=11.0 Hz, 1H), 3.55 (d, J=11.0 Hz 1H), 3.38-3.48 (m, 2H), 3.04-3.2 (m, 3H), 2.79 (d, J=9.1 Hz, 1H), 2.48 (d, J=9.1 Hz, 1H), 1.55-2.01 (m, 8H), 1.04-1.44 (m, 6H).
HRMS (ESI+): calcd. for $C_{20}H_{29}N_2O_4$ [M+H]$^+$ 361.2122; found 361.2129.

Step o

3-Oxo-2-piperidin-4-yl-2,3-dihydro-1H-isoindole-4-carboxylic acid hydrochloride (XIX) [n=0; R1=piperidin-4-yl]

3-(1-Tert-butoxycarbonyl-piperidin-4-yl)-4-oxo-10-oxa-3-aza-tricyclo[5.2.1.0*1,5*]dec-8-ene-6-carboxylic acid (XVII) (6.35 g, 16.8 mmol) was dissolved in 37% hydrochloric acid (80 mL) and the resulted solution was refluxed for 3 h. The solvent was removed under reduced pressure and the residue was diluted with methanol and decanted to obtain the desired product (XIX) as a white solid (4.06 g, 82%).

$^1$H NMR (400.5 MHz, DMSO-d$_6$) δ ppm 1.95-2.12 (m, 4H), 3.01-3.18 (m, 2H), 3.36-3.45 (m, 2H), 4.36-4.46 (m, 1H), 4.72 (s, 2H), 7.85 (dd, J=7.7, 7.5 Hz, 1H), 7.95 (dd, J=7.5, 0.8 Hz, 1H), 8.17 (dd, J=7.7, 0.8 Hz, 1H), 8.53 (br. s., 1H), 8.79 (br. s., 1H), 15.86 (s, 1H).

HRMS (ESI+): calcd. for $C_{14}H_{17}N_2O_3$ [M+H]$^+$ 261.1234; found 261.1222.

Operating in an analogous way, but employing suitably substituted starting material (XVII) the following compounds were obtained:

2-Benzyl-3-oxo-2,3-dihydro-1H-isoindole-4-carboxylic acid (XVIII)
HRMS (ESI+): calcd. for $C_{16}H_{14}NO_3$ [M+H]$^+$ 268.0968; found 268.0972.

3-Oxo-2-phenethyl-2,3-dihydro-1H-isoindole-4-carboxylic acid (XVIII)
HRMS (ESI+): calcd. for $C_{17}H_{35}NO_3$ [M+H]$^+$ 282.1125; found 282.1131.

2-[2-(3,4-Dihydro-1H-isoquinolin-2-yl)-ethyl]-3-oxo-2,3-dihydro-1H-isoindole-4-carboxylic acid (XVIII)
HRMS (ESI+): calcd. for $C_{20}H_{21}N_2O_3$ [M+H]$^+$ 337.1547; found 337.1541.

3-Oxo-2-(2-piperidin-1-yl-ethyl)-2,3-dihydro-1H-isoindole-4-carboxylic acid (XVIII)
HRMS (ESI+): calcd. for $C_{16}H_{21}N_2O_3$ [M+H]$^+$ 288.1547; found 288.1552.

2-(2-Morpholin-4-yl-ethyl)-3-oxo-2,3-dihydro-1H-isoindole-4-carboxylicacid (XVIII)
HRMS (ESI+): calcd. for $C_{15}H_{19}N_2O_4$ [M+H]$^+$ 291.1339; found 291.1335.

2-(3-Morpholin-4-yl-propyl)-3-oxo-2,3-dihydro-1H-isoindole-4-carboxylic acid (XVIII)
HRMS (ESI+): calcd. for $C_{15}H_{21}N_2O_4$ [M+H]$^+$ 305.1496; found 305.1492.

2-[2-(3,4-Dihydro-2H-quinolin-1-yl)-ethyl]-3-oxo-2,3-dihydro-1H-isoindole-4-carboxylicacid (XVIII)
HRMS (ESI+): calcd. for $C_{20}H_{21}N_2O_3$ [M+H]$^+$ 337.1547; found 337.1549.

3-Oxo-2-(3-phenyl-propyl)-2,3-dihydro-1H-isoindole-4-carboxylic acid (XVIII)
HRMS (ESI+): calcd. for $C_{18}H_{18}NO_3$ [M+H]$^+$ 296.1281; found 296.1290.

3-Oxo-2-(2-pyridin-2-yl-ethyl)-2,3-dihydro-1H-isoindole-4-carboxylicacid (XVIII)
HRMS (ESI+): calcd. for $C_{16}H_{15}N_2O_3$ [M+H]$^+$ 283.1077; found 283.1080.

2-[3-(3,4-Dihydro-1H-isoquinolin-2-yl)-propy]-3-oxo-2,3-dihydro-1H-isoindole-4-carboxylicacid (XVIII)
HRMS (ESI+): calcd. for $C_{21}H_{23}N_2O_3$ [M+H]$^+$ 351.1703; found 351.1706.

2-[3-(3,4-Dihydro-2H-quinolin-1-yl)-propyl]-3-oxo-2,3-dihydro-1H-isoindole-4-carboxylicacid (XVIII)
HRMS (ESI+): calcd. for $C_{21}H_{23}N_2O_3$ [M+H]$^+$ 351.1703; found 351.1699.

2-[3-(4-Methyl-piperazin-1-yl)-propyl]-3-oxo-2,3-dihydro-1H-isoindole-4-carboxylic acid (XVIII)
HRMS (ESI+): calcd. for $C_{17}H_{24}N_3O_3$ [M+H]$^+$ 318.1812; found 318.1820.

3-Oxo-2-[3-(4-phenyl-piperazin-1-yl)-propy]-2,3-dihydro-1H-isoindole-4-carboxylic acid (XVIII)
HRMS (ESI+): calcd. for $C_{22}H_{26}N_3O_3$ [M+H]$^+$ 380.1969; found 380.1971.

3-Oxo-2-(3-piperidin-1-yl-propyl)-2,3-dihydro-1H-isoindole-4-carboxylic acid (XVIII)
HRMS (ESI+): calcd. for $C_{17}H_{23}N_2O_3$ [M+H]$^+$ 303.1703; found 303.1702.

2-(3-[1,4']Bipiperidinyl-1'-yl-propyl)-3-oxo-2,3-dihydro-1H-isoindole-4-carboxylic acid (XVIII)
HRMS (ESI+): calcd. for $C_{22}H_{32}N_3O_3$ [M+H]$^+$ 386.2438; found 386.2442.

2-[3-(2,6-Dimethyl-piperidin-1-yl)-propyl]-3-oxo-2,3-dihydro-1H-isoindole-4-carboxylic acid (XVIII)
HRMS (ESI+): calcd. for $C_{19}H_{27}N_2O_3$ [M+H]$^+$ 331.2016; found 331.2011.

3-Oxo-2-[1-(tetrahydro-pyran-4-yl)-piperidin-4-yl)-2,3-dihydro-1H-isoindole-4-carboxylicacid (XVIII)
HRMS (ESI+): calcd. for $C_{21}H_{23}N_2O_4$ [M+H]$^+$ 345.1809; found 345.1816.

2-(1-Benzyl-piperidin-4-yl)-3-oxo-2,3-dihydro-1H-isoindole-4-carboxylic acid (XVIII)
HRMS (ESI+): calcd. for $C_{21}H_{23}N_2O_3$ [M+H]$^+$ 351.1703; found 351.1708.

2-[2-(1-Benzyl-piperidin-4-yl)-ethyl]-3-oxo-2,3-dihydro-1H-isoindole-4-carboxylic acid (XVIII)
HRMS (ESI+): calcd. for $C_{23}H_{27}N_2O_3$ [M+H]$^+$ 379.2016; found 379.2020.

2-[3-(4-Benzyl-piperidin-1-yl)-propy]-3-oxo-2,3-dihydro-1H-isoindole-4-carboxylic acid (XVIII)
HRMS (ESI+): calcd. for $C_{24}H_{29}N_2O_3$ [M+H]$^+$ 393.2173; found 393.2177.

2-(1-Cyclohexyl-piperidin-4-yl)-3-oxo-2,3-dihydro-1H-isoindole-4-carboxylicacid (XVIII)
HRMS (ESI+): calcd. for $C_{20}H_{27}N_2O_3$ [M+H]$^+$ 343.2016; found 343.2019.

Step q 2-(1-Tert-butoxycarbonyl-piperidin-4-yl)-3-oxo-2,3-dihydro-1H-isoindole-4-carboxylic acid (XVIII)
[n=0; R1=piperidin-4-yl; X=tert-butoxycarbonyl]

To a solution of 3-oxo-2-piperidin-4-yl-2,3-dihydro-1H-isoindole-4-carboxylic acid (3.9 g, 13.2 mmol) in pyridine (15 mL) potassium carbonate (3.6 g, 26.5 mmol) and methanol (40 mL) were successively added. Then di-tert-butyl dicarbonate (3.16 g, 14.5 mmol) was added and the reaction mixture was stirred at room temperature for 4 h until HPLC analysis revealed the disappearance of the starting material. The solvent was removed under reduced pressure and the residue was dissolved in dichloromethane. The solution was washed twice with 5% potassium hydrogen sulfate and the organic phase was dried over Na$_2$SO$_4$ and concentrated in vacuo. The obtained crude wad diluted with diethyl ether and decanted to obtain the title compound (3.7 g, 78%) as a white solid.

$^1$H NMR (400.5 MHz, DMSO-d$_6$) δ ppm 1.42 (s, 9H), 1.04-1.74 (m, 2H), 1.80-1.88 (m, 2H), 2.89 (br. s., 2H), 4.04-4.12 (m, 2H), 4.23-4.32 (m, 1H), 4.73 (s, 2H), 7.83 (dd, J=7.5, 0.8 Hz, 1H), 7.91 (dd, J=7.5, 0.8 Hz, 1H), 8.17 (dd, J=7.7, 0.8 Hz, 1H), 16.03 (br. s., 1H).

Step p 4-(7-Carbamoyl-1-oxo-1,3-dihydro-isoindol-2-yl)-piperidine-1-carboxylic acid tert-butyl ester (XX)
[n=0; R1=piperidin-4-yl; X=tert-butoxycarbonyl]

Method A: to a solution of 2-(1-tert-butoxycarbonyl-piperidin-4-yl)-3-oxo-2,3-dihydro-1H-isoindole-4-carboxylic acid (XVIII) (3.7 g, 10.3 mmol) in N,N-dimethylformamide (60 mL) hydroxybenzotriazole ammonium salt (3.15 g, 20.7 mmol), 1-ethyl-3-(3'-dimethylamino)carbodiimide hydrochloric acid salt (3.34 g, 20.7 mmol) and disopropylethylamine (5.3 ml, 30.9 mmol) were added. The reaction mixture was stirred at room temperature overnight. The solvent was removed under reduced pressure and the residue was dissolved in ethyl acetate. The solution was washed twice with saturated sodium carbonate aqueous solution, and the organic phase was dried over anhydrous sodium sulfate and concentrated in vacuo. The crude was purified by lash chromatography (dichloromethane/methanol 97:3) to afford the title compound (2.74 g, 74%) as a white solid.

Method B: a solution of 2-(1-tert-butoxycarbonyl-piperidin-4-yl)-2,3-dihydro-1H-isoindole-4-carboxylic acid (XVIII) (5.5 g, 15.3 mmol) and carbonyldiimidazole (3.7 g, 22.8 mmol) in dry tetrahydrofuran (80 ml) was stirred at room temperature for 4 h. Then concentrated aqueous ammonia (25 ml) was added and the reaction mixture was left at room temperature until the disappearance of the starting material (3 h). The solvent was evaporated under reduced pressure and the resulting crude primary amide (1.1 g, 20%) was employed without any further purification.

HRMS (ESI+): calcd. for $C_{19}H_{26}N_3O_4$ [M+H]$^+$ 360.1918; found 360.1921.

Operating according to method A, but employing suitably substituted starting material the following compounds were obtained:

2-benzyl-3-oxo-2,3-dihydro-1H-isoindole-4-carboxylic acid amide (I), cpd 1
[R=H; n=1; R1=phenyl; m=0; R2=null]

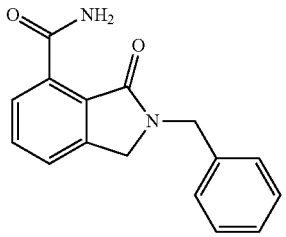 [SMILES: NC(=O)c1cccc2c1C(=O)N(Cc1ccccc1)C2]

$^1$H NMR (400.5 MHz, DMSO-A) δ ppm 1.72-1.88 (m, 4H), 2.04-2.13 (m, 2H), 2.88-2.96 (m, 2H), 3.51 (s, 2H), 4.00-4.11 (m, 1H), 4.56 (s, 2H), 7.20-7.30 (m, 1H), 7.31-7.37 (m, 4H), 7.66 (br. s., 1H), 7.71 (dd, J=7.6, 7.4 Hz, 1H), 7.76 (dd, J=7.6, 1.5 Hz, 1H), 8.20 (dd, J=7.4, 1.5 Hz, 1H), 10.72 (br. s., 1H).

HRMS (ESI+): calcd. for $C_{16}H_{15}N_2O_2$ [M+H]$^+$ 267.1128; found 267.1120.

3-oxo-2-phenethyl-2,3-dihydro-1H-isoindole-4-carboxylic acid amide (I), cpd 2
[R=H; n=2; R1=phenyl; m=0; R2=null]

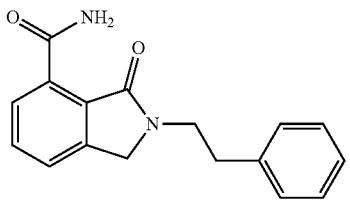 [SMILES: NC(=O)c1cccc2c1C(=O)N(CCc1ccccc1)C2]

$^1$H NMR (400.5 MHz, DMSO-d$_6$) δ ppm 2.97 (t, J=7.6 Hz, 2H), 3.82 (t, J=7.6 Hz, 2H), 4.49 (s, 2H), 7.17-7.24 (m, 1H), 7.24-7.32 (m, 4H), 7.66 (br. s., 1H), 7.70 (dd, J=7.5, 7.3 Hz, 1H), 7.74 (dd, J=7.5, 1.5 Hz, 1H), 8.19 (dd, J=7.3, 1.5 Hz, 1H), 10.68 (br. s., 1H).

HRMS (ESI+): calcd. for $C_{17}H_{15}N_2O_2$ [M+H]$^+$ 281.1285; found 281.1295.

2-[2-(3,4-dihydro-1H-isoquinolin-2-yl)-ethyl]-3-xo-2,3-dihydro-1H-isoindole-4-carboxylic acid amide (I), cpd 3
[R=H; n=2; R1=3,4-dihydro-1H-isoquinolin-2-yl; m=0; R2=null]

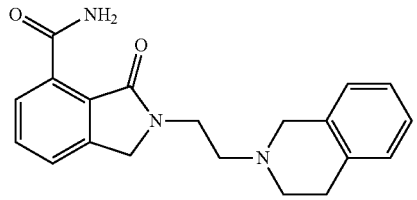 [SMILES: NC(=O)c1cccc2c1C(=O)N(CCN1CCc3ccccc3C1)C2]

$^1$H NMR (400.5 MHz, DMSO-d$_6$) δ ppm 2.73-2.84 (m, 6H), 3.65 (s, 2H), 3.81 (t, J=6.2 Hz, 2H), 4.65 (s, 2H), 7.00-7.12 (m, 4H), 7.66 (br. s., 1H), 7.69 (dd, J=7.6, 7.7 Hz, 1H), 7.76 (dd, J=7.6, 1.2 Hz, 1H), 8.19 (dd, J=7.7, 1.2 Hz, 1H), 10.75 (br. s., 1H).

HRMS (ESI+): calcd. for $C_{20}H_{23}N_3O_2$ [M+H]$^+$ 336.1707; found 336.1722.

3-oxo-2-(2-piperidin-1-yl-ethyl)-2,3-dihydro-1H-isoindole-4-carboxylic acid amide (I), cpd 4
[R=H; n=2; R1=piperidin-1-yl; m=0; R2=null]

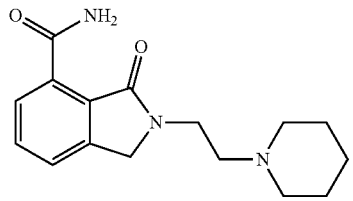 [SMILES: NC(=O)c1cccc2c1C(=O)N(CCN1CCCCC1)C2]

$^1$H NMR (400.5 MHz, DMSO-d$_6$) δ ppm 1.33-1.40 (m, 2H), 1.43-1.50 (m, 4H), 2.35-2.43 (m, 4H), 2.54 (t, J=6.3 Hz, 2H), 3.68 (t, J=6.3 Hz, 2H), 4.63 (s, 2H), 7.66 (br. s., 1H), 7.72 (dd, J=7.7, 7.4 Hz, 1H), 7.78 (dd, J=7.4, 1.2 Hz, 1H), 8.20 (dd, J=7.7, 1.2 Hz, 1H), 10.75 (br. s., 1H).

HRMS (ESI+): calcd. for $C_{16}H_{22}N_3O_2$ [M+H]$^+$ 288.1707; found 288.1712.

2-(2-morpholin-4-yl-ethyl)-3-oxo-2,3-dihydro-1H-isoindole-4-carboxylic acid amide (I), cpd 5
[R=H; n=2; R1=morpholin-4-yl; m=0; R2=null]

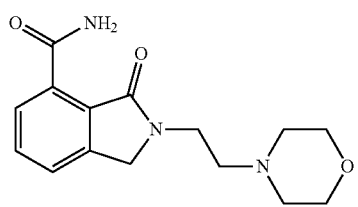 [SMILES: NC(=O)c1cccc2c1C(=O)N(CCN1CCOCC1)C2]

$^1$H NMR (400.5 MHz, DMSO-d$_6$) δ ppm 2.41-2.46 (m, 4H), 2.59 (t, J=6.3 Hz, 2H), 3.52-3.57 (m, 4H), 3.71 (t, J=6.3 Hz, 2H), 4.64 (s, 2H), 7.66 (br. s., 1H), 7.72 (dd, J=7.7, 7.6 Hz, 1H), 7.78 (dd, J=7.6, 1.3 Hz, 1H), 8.20 (dd, J=7.7, 1.3 Hz, 1H), 10.73 (br. s., 1H).

HRMS (ESI+): calcd. for $C_{15}H_{20}N_3O_3$ [M+H]$^+$ 290.1499; found 290.1507.

2-(3-morpholin-4-yl-propyl-3-oxo-2,3-dihydro-1H-isoindole-4-carboxylic acid amide (I), cpd 6

[R=H; n=3; R1=morpholin-4-yl; m=0; R2=null]

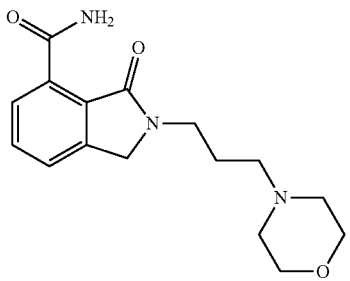 [SMILES: NC(=O)c1cccc2c1C(=O)N(CCCN1CCOCC1)C2]

$^1$H NMR (400.5 MHz, DMSO-d$_6$) δ ppm 1.80 (quintet, J=7.1 Hz, 2H), 2.28-2.38 (m, 6H), 3.47-3.54 (m, 4H), 3.61 (t, J=7.1 Hz, 2H), 4.58 (s, 2H), 7.65 (br. s., 1H), 7.71 (dd, J=7.6, 7.4 Hz, 1H), 7.77 (dd, J=7.4, 1.2 Hz, 1H), 8.20 (dd, J=7.6, 1.2 Hz, 1H), 10.76 (br. s., 1H).

HRMS (ESI+): calcd. for $C_{16}H_{22}N_3O_3$ [M+H]$^+$ 304.1656; found 304.1664.

2-[2-(3,4-dihydro-2H-quinolin-1-yl)-ethyl]-3-oxo-2,3-dihydro-1H-isoindole-4-carboxylic acid amide (I), cpd 7

[R=H; n=2; R1=3,4-dihydro-2H-quinolin-1-yl; m=0; R2=null]

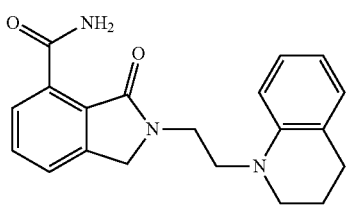 [SMILES: NC(=O)c1cccc2c1C(=O)N(CCN1CCCc3ccccc31)C2]

$^1$H NMR (400.5 MHz, DMSO-d$_6$) δ ppm 1.79-1.89 (m, 2H), 2.64-2.70 (m, 2H), 3.27-3.31 (m, 2H), 3.56 (t, J=7.1 Hz, 2H), 3.76 (t, J=7.1 Hz, 2H), 4.65 (s, 2H), 6.44-6.49 (m, 1H), 6.70-6.75 (m, 1H), 6.85-6.89 (m, 1H), 6.92-6.97 (m, 1H), 7.69 (br. s., 1H), 7.72 (dd, J=7.6, 7.6 Hz, 1H), 7.77 (dd, J=7.6, 1.3 Hz, 1H), 8.20 (dd, J=7.6, 1.3 Hz, 1H), 10.68 (br. s., 1H).

HRMS (ESI+): calcd. for $C_{20}H_{22}N_3O_2$ [M+H]$^+$ 336.1707; found 336.1692.

3-oxo-2-(3-phenyl-propyl)-2,3-dihydro-1H-isoindole-4-carboxylic acid amide (I), cpd 17

[R=H; n=3; R1=phenyl; m=0; R2=null]

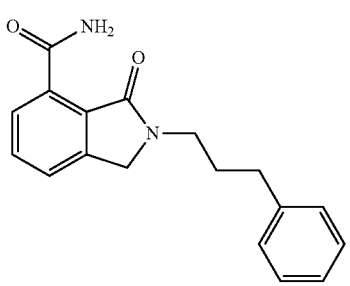 [SMILES: NC(=O)c1cccc2c1C(=O)N(CCCc1ccccc1)C2]

$^1$H NMR (400.5 MHz, DMSO-d$_6$) δ ppm 1.97 (quintet, J=7.9 Hz, 2H), 2.64 (t, J=7.9 Hz 2H), 3.61 (t, J=7.9 Hz, 2H), 4.59 (s, 2H), 7.15-7.20 (m, 1H), 7.23-7.31 (m, 4H), 7.67 (br. s., 1H), 7.72 (dd, J=7.6, 7.4 Hz, 1H), 7.77 (dd, J=7.6, 1.5 Hz, 1H), 8.21 (dd, J=7.4, 1.5 Hz, 1H), 10.74 (br. s., 1H).

HRMS (ESI+): calcd. for $C_{18}H_{19}N_2O_2$ [M+H]$^+$ 295.1441; found 295.1433.

3-oxo-2-(2-pyridin-2-yl-ethyl)-2,3-dihydro-1H-isoindole-4-carboxylic acid amide (I), cpd 18

[R=H; n=2; R1=pyrid-2-yl; m=0; R2=null]

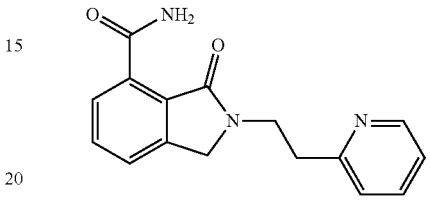

$^1$H NMR (400.5 MHz, DMSO-d$_6$) δ ppm 3.12 (t, J=7.3 Hz, 2H), 3.96 (t, J=7.3 Hz, 2H), 4.52 (s, 2H), 7.23 (ddd, J=7.5, 4.9, 1.2 Hz, 1H), 7.32 (ddd, J=7.8, 1.2, 0.8 Hz, 1H), 7.65 (br. s., 1H), 7.71 (m, 1H), 7.70 (dd, J=7.6, 7.4 Hz, 1H), 7.75 (dd, J=7.6, 1.3 Hz, 1H), 8.19 (dd, J=7.4, 1.3 Hz, 1H), 8.48 (ddd, J=4.9, 1.8, 0.8 Hz, 1H), 10.66 (br. s., 1H).

HRMS (ESI+): calcd. for $C_{16}H_{16}N_3O_2$ [M+H]$^+$ 282.1237; found 282.1243.

2-[3-(3,4-dihydro-1H-isoquinolin-2-yl)-propyl]-3-oxo-2,3-dihydro-1H-isoindole-4-carboxylic acid amide (I), cpd 19

[R=H; n=3; R1=3,4-dihydro-1H-isoquinolin-2-yl; m=0; R2=null]

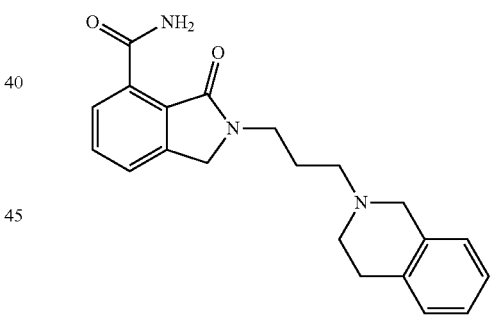

$^1$H NMR (400.5 MHz, DMSO-d$_6$) δ ppm 1.92 (quintet, J=7.3 Hz, 2H), 2.52 (t, J=7.3 Hz, 2H), 2.64-2.70 (m, 2H), 2.76-2.82 (m, 2H), 3.57 (s, 2H), 3.64 (t, J=7.3 Hz, 2H), 4.60 (s, 2H), 7.00-7.70 (m, 4H), 7.66 (br. s., 1H), 7.70 (dd, J=7.6, 7.4 Hz, 1H), 7.75 (dd, J=7.4, 1.3 Hz, 1H), 8.19 (dd, J=7.6, 1.3 Hz, 1H), 10.76 (br. s., 1H).

HRMS (ESI+): calcd. for $C_{21}H_{24}N_3O_2$ [M+H]$^+$ 350.1863; found 350.1866.

2-[3-(3,4-dihydro-2H-quinolin-1-yl)-propyl]-3-oxo-2,3-dihydro-1H-isoindole-4-carboxylic acid amide (I), cpd 20

[R=H; n=3; R1=3,4-dihydro-2H-quinolin-1-yl; m=0; R2=null]

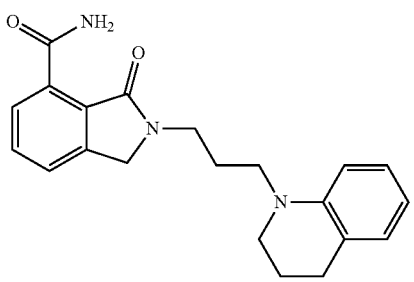 [SMILES: NC(=O)c1cccc2c1C(=O)N(CCCN1CCCc3ccccc31)C2]

¹H NMR (400.5 MHz, DMSO-d₆) δ ppm 1.80-1.87 (m, 2H), 1.90 (quintet, J=7.2 Hz, 2H), 2.65 (t, J=7.2 Hz, 2H), 3.22-3.26 (m, 2H), 3.27-3.30 (m overlapped by water signal, 2H), 3.64 (t, J=7.2 Hz, 2H), 4.59 (s, 2H), 6.42-6.47 (m, 1H), 6.54-6.58 (m, 1H), 6.83-6.87 (m, 1H), 6.89-6.94 (m, 1H), 7.67 (br. s., 1H), 7.72 (dd, J=7.6, 7.6 Hz, 1H), 7.77 (dd, J=7.6, 1.3 Hz, 1H), 8.20 (dd, J=7.6, 1.3 Hz, 1H), 10.72 (br. s., 1H).

HRMS (ESI+): calcd. for $C_{21}H_{24}N_3O_2$ [M+H]⁺ 350.1863; found 350.1868.

2-[3-(4-methyl-piperazin-1-yl)-propyl]-3-oxo-2,3-dihydro-1H-isoindole-4-carboxylic acid amide (I), cpd 21

[R=H; n=3; R1=4-methyl-piperazin-1-yl; m=0; R2=null]

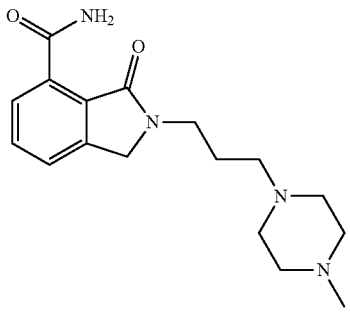 [SMILES: CN1CCN(CCCN2Cc3cccc(C(N)=O)c3C2=O)CC1]

¹H NMR (400.5 MHz, DMSO-d₄) δ ppm 1.80 (quintet, J=7.2 Hz, 2H), 2.11 (s, 3H), 2.15-2.43 (br. s., 8H), 2.33 (t, J=7.2 Hz, 2H), 3.60 (t, J=7.2 Hz, 2H), 4.58 (s, 2H), 7.66 (br. s., 1H), 7.72 (dd, J=7.6, 7.4 Hz, 1H), 7.77 (dd, J=7.6, 1.3 Hz, 1H), 8.21 (dd, J=7.4, 1.3 Hz, 1H), 10.79 (br. s., 1H).

HRMS (ESI+): calcd. for $C_{17}H_{25}N_4O_2$ [M+H]⁺ 317.1972; found 317.1975.

3-oxo-2-[3-(4-phenyl-piperazin-1-yl)-propyl]-2,3-dihydro-1H-indole-4-carboxylic acid amide (I), cpd 22

[R=H; n=3; R1=piperazin-1-yl; m=0; R2=4-phenyl]

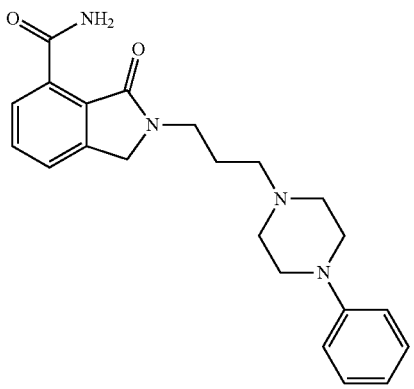 [SMILES: NC(=O)c1cccc2c1C(=O)N(CCCN1CCN(c3ccccc3)CC1)C2]

¹H NMR (400.5 MHz, DMSO-d₄) δ ppm 1.85 (quintet, J=7.1 Hz, 2H), 2.39 (t, J=7.1 Hz, 2H), 3.02-3.10 (m, 4H), 3.63 (t, J=7.1 Hz, 2H), 4.60 (s, 2H), 6.75 (t, J=7.3 Hz, 1H), 6.89 (d, J=7.9 Hz, 2H), 7.19 (dd, J=7.9, 7.3 Hz, 2H), 7.66 (br. s., 1H), 7.70 (dd, J=7.7, 7.4 Hz, 1H), 7.76 (dd, J=7.4, 1.2 Hz, 1H), 8.20 (dd, J=7.7, 1.2 Hz, 1H), 10.78 (br. s., 1H).

HRMS (ESI+): calcd. for $C_{22}H_{27}N_4O_2$ [M+H]⁺ 379.2129; found 379.2145.

3-oxo-2-(3-piperidin-1-vi-propyl-2,3-dihydro-1H-isoindole-4-carboxylic acid amide hydrochloride (I), cpd 25

[R=H; n=3; R1=piperidin-1-yl; m=0; R2=null]

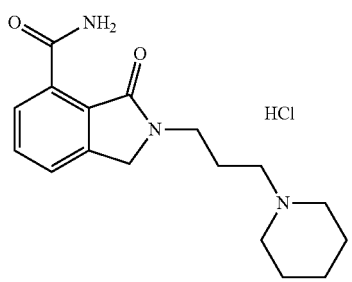 [SMILES: NC(=O)c1cccc2c1C(=O)N(CCCN1CCCCC1)C2 ; Cl]

¹H NMR (400.5 MHz, DMSO-d₆) δ ppm 1.29 (m, 1H), 1.50-1.73 ((m, 3H), 1.75-1.85 ((m, 2H), 2.00-2.09 (m, 2H), 2.79-2.92 (m, 2H), 3.03-3.14 (m, 2H), 3.40-3.50 (m, 2H), 3.66 (t, J=6.6 Hz, 2H), 4.59 (s, 2H), 7.71 (br. s., 1H), 7.74 (dd, J=7.6, 7.4 Hz, 1H), 7.80 (dd, J=7.4, 1.1 Hz, 1H), 8.21 (dd, J=7.6, 1.1 Hz, 1H), 8.93 (br. s., 1H), 10.58 (br. s., 1H).

HRMS (ESI+): calcd. for $C_{17}H_{24}N_3O_2$ [M+H]⁺ 302.1863; found 302.1865.

2-(3-[1,4']bipiperidinyl-1'-yl-propyl)-3-oxo-2,3-dihydro-1H-isoindole-4-carboxylic acid amide dihydrochloride (I), cpd 26

[R=H; n=3; R1=piperidin-1-yl; m=0; R2=4-piperidin-1-yl]

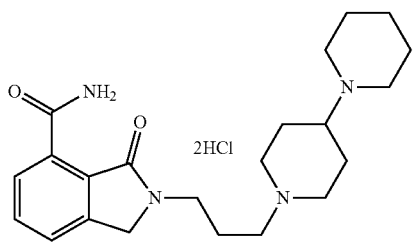 [SMILES: NC(=O)c1cccc2c1C(=O)N(CCCN1CCC(N3CCCCC3)CC1)C2]

¹H NMR (400.5 MHz, DMSO-d₆) δ ppm 1.33-1.49 (m, 1H), 1.57-1.74 (m, 3H), 1.74-1.94 (m, 4H), 1.95-2.13 (m, 2H), 2.16-2.30 (m, 2H), 2.87-3.72 (m, 11H), 3.66 (t, J=6.5 Hz, 2H), 4.59 (s, 2H), 7.72 (br. s., 1H), 7.75 (dd, J=7.6, 6.7 Hz, 1H), 7.80 (d, J=6.7 Hz, 1H), 8.21 (dd, J=7.6, 1.2 Hz, 1H), 9.38 (br. s., 2H), 10.58 (br. s., 1H).

HRMS (ESI+): calcd. for $C_{22}H_{33}N_4O_2$ [M+H]⁺ 385.2598; found 385.2611.

2-[3-(2,6-dimethyl-piperidin-1-yl)-propyl]-3-oxo-2,3-dihydro-1H-isoindole-4-carboxylic acid amide hydrochloride (I), cpd 27

[R=H; n=3; R1=2,6-dimethyl-piperidin-1-yl; m=0; R2=null]

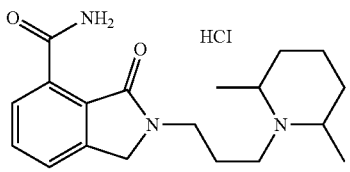

¹H NMR (400.5 MHz, DMSO-d₆) δ ppm 1.25 (d, J=6.3 Hz, 6H), 1.40-1.55 (m, 3H), 1.80-1.91 (m, 2H), 1.95-2.05 (m, 2H), 3.02-3.46 (m, 4H), 3.68 (m, 2H), 4.63 (s, 2H), 7.70 (br. s., 1H), 7.74 (dd, J=7.6, 7.6 Hz, 1H), 7.80 (dd, J=7.6, 1.2 Hz, 1H), 8.21 (dd, J=7.6, 1.2 Hz, 1H), 8.72 (br. s., 1H), 10.58 (br. s., 1H).

HRMS (ESI+): calcd. for $C_{19}H_{28}N_3O_2$ [M+H]⁺ 330.2176; found 330.2176.

3-oxo-2-[1-(tetrahydro-pyran-4-yl]-piperidin-4-yl-2,3-dihydro-1H-isoindole-4-carboxylicacid amide (I), cpd 28

[R=H; n=m=0; R1=piperidin-4-yl; R2=1-(tetrahydro-pyran-4-yl)]

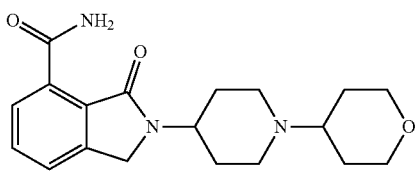 [SMILES: NC(=O)c1cccc2c1C(=O)N(C1CCN(C3CCOCC3)CC1)C2]

¹H NMR (400.5 MHz, DMSO-d₆) δ ppm 1.38-1.50 (m, 2H), 1.65-1.72 (m, 2H), 1.73-1.81 (m, 4H), 2.18-2.28 (m, 2H), 2.43-2.47 (m, 1H), 2.97-3.04 (m, 2H), 3.30 (m overlapped by water signal, 2H), 3.89 (dd, J=11.1, 3.9 Hz, 2H), 4.02 (m, 1H), 4.55 (a, 2H), 7.66 (br. s., 1H), 7.71 (dd, J=7.6, 7.4 Hz, 1H), 7.76 (dd, J=7.4, 1.5 Hz, 1H), 8.20 (dd, J=7.6, 1.5 Hz, 1H), 10.74 (br. s., 1H).

HRMS (ESI+): calcd. for $C_{19}H_{26}N_3O_3$ [M+H]⁺ 344.1969; found 344.1962.

2-(1-ben piperidin-4-yl)-3-oxo-2,3-dihydro-1H-isoindole-4-carboxylic acid amide (I), cpd 30

[R=H; n=0; R1=piperidin-4-yl; m=1; R2=phenyl]

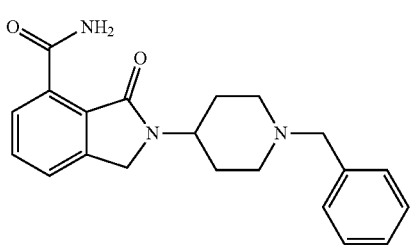 [SMILES: NC(=O)c1cccc2c1C(=O)N(C1CCN(Cc3ccccc3)CC1)C2]

¹H NMR (400.5 MHz, DMSO-d₆) δ ppm 1.70-1.88 (m, 4H), 1.99-2.13 (m, 2H), 2.89-2.96 (m, 2H), 3.51 (s, 2H), 4.00-4.11 (m, 1H), 4.56 (s, 2H), 720-7.30 (m, 1H), 7.30-7.36 (m, 4H), 7.66 (br. s., 1H), 7.71 (dd, J=7.6, 7.4 Hz, 1H), 7.76 (dd, J=7.6, 1.5 Hz, 1H), 8.20 (dd, J=7.4, 1.5 Hz, 1H), 10.72 (br. s., 1H).

HRMS (ESI+): calcd. for $C_{21}H_{24}N_3O_2$ [M+H]⁺ 350.1863; found 350.1874.

2-[2-(1-benzyl-piperidin-4-yl)-ethyl]-3-oxo-2,3-dihydro-1H-isoindole-4-carboxylic acid amide hydrochloride (I), cpd 31

[R=H; n=2; R1=piperidin-4-yl; m=1; R2=phenyl]

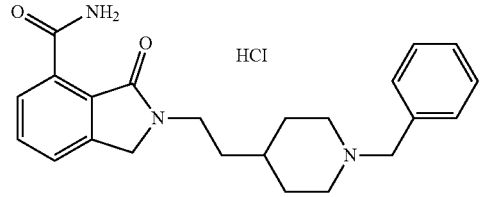 [SMILES: NC(=O)c1cccc2c1C(=O)N(CCC1CCN(Cc3ccccc3)CC1)C2 ; "HCI"]

¹H NMR (400.5 MHz, DMSO-d₆) δ ppm 1.29-1.41 (m, 2H), 1.43-1.54 (m, 1H), 1.56-1.64 (m, 2H), 1.92-2.00 (m, 2H), 2.83-2.96 (m, 2H), 3.30 (m overlapped by water signal, 2H), 3.61 (t, J=6.8 Hz, 2H), 4.25 (d, J=5.1 Hz, 2H), 4.57 (s, 2H), 7.47 (s, 5H), 7.69 (br. s., 1H), 7.72 (dd, J=7.6, 7.4 Hz, 1H), 7.77 (dd, J=7.4, 1.3 Hz, 1H), 8.20 (dd, J=7.6, 1.3 Hz, 1H), 9.22 (br. s., 1H), 10.68 (br. s., 1H).

HRMS (ESI+): calcd. for $C_{23}H_{28}N_3O_2$ [M+H]⁺ 378.2176; found 378.2178.

2-[3-(4-benzyl-piperidin-1-yl)-propyl]-3-oxo-2,3-dihydro-1H-isoindole-4-carboxylic acid amide (I), cpd 32

[R=H; n=3; R1=piperidin-1-yl; m=1; R2=phenyl]

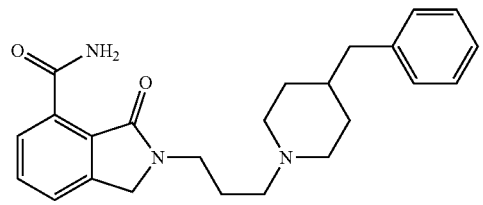 [SMILES: NC(=O)c1cccc2c1C(=O)N(CCCN1CCC(Cc3ccccc3)CC1)C2]

¹H NMR (400.5 MHz, DMSO-d₆) δ ppm 0.93-1.12 (m, 2H), 1.34-1.53 (m, 3H), 1.68-1.82 (m, 4H), 2.22-2.33 (m, 2H), 2.41 (d, J=6.8 Hz, 2H), 2.75-2.85 (m, 2H), 3.59 (t, J=6.9 Hz, 2H), 4.56 (s, 2H), 7.09-7.14 (m, 2H), 7.14-7.19 (m, 1H), 7.23-7.29 (m, 2H), 7.65 (br. s., 1H), 7.72 (dd, J=7.4, 7.4 Hz, 1H), 7.77 (dd, J=7.4, 1.3 Hz, 1H), 8.21 (dd, J=7.4, 1.3 Hz, 1H), 10.78 (br. s., 1H).

HRMS (ESI+): calcd. for $C_{24}H_{30}N_3O_2$ [M+H]⁺ 392.2333; found 392.2346.

Step i'

3-Oxo-2-piperidin-4-yl-2,3-dihydro-1H-isoindole-4-carboxylic acid amide hydrochloride (XXI)

[n=0; R1=piperidin-4-yl]

A solution of 4-(7-carbamoyl-1-oxo-1,3-dihydro-isoindol-2-yl)-piperidine-1-carboxylic acid tert-butyl ester (XX) (2.7 g, 7.5 mmol) in 4M hydrochloric acid in dioxane (18 mL, 75 mmol) was stirred at 50° C. for 2 h until HPLC analysis revealed the disappearance of the starting material. The solvent was removed under reduced pressure and the product was dissolved in diethyl ether and filtered to obtain the title compound (2.09 g, 95%) as its hydrochloride. ¹H NMR (400.5 MHz, DMSO-d₆) δ ppm 1.93-2.09 (m, 4H), 3.03-3.17 (m, 2H), 3.35-3.48 (m overlapped by water signal, 2H), 4.32-4.45 (m, 1H), 4.56 (s, 2H), 7.71 (br. s., 1H), 7.75 (dd, J=7.5, 7.5 Hz, 1H), 7.82 (dd, J=7.5, 1.1 Hz 1H), 8.21 (dd, J=7.5, 1.1 Hz, 1H), 8.59 (br.s., 1H), 8.82 (br. s., 1H), 10.58 (br. s., 1H).

HRMS (ESI+): calcd. for $C_{14}H_{18}N_3O_2$ [M+H]$^+$ 260.1394; found 260.1398.

Step l'

2-(1-cyclohexyl-piperidin-4-yl)-3-oxo-2,3-dihydro-1H-isoindole-4-carboxylic acid amide (I), cpd 11

[R=H; n=m=0; R1=piperidin-4-yl; R2=1-cyclohexyl]

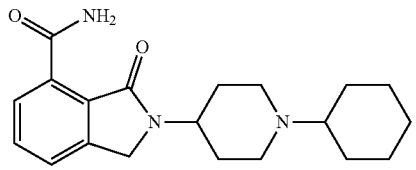 [SMILES: NC(=O)c1cccc2c1C(=O)N(C1CCN(C3CCCCC3)CC1)C2]

Method A: to a suspension of 3-oxo-2-piperidin-4-yl-2,3-dihydro-1H-isoindole-4-carboxylic acid amide hydrochloride (56 mg, 0.19 mmol) in dichloromethane (2 mL), cyclohexanone (XIV) (27.5 mg, 0.28 mmol), sodium acetate (32 mg, 0.38 mmol) and methanol (0.3 mL) were added. The resultant solution was stirred at room temperature for 5 h. Then sodium cyanoborohydride (13 mg, 0.21 mmol) was added and the mixture was stirred overnight Solvents were removed under reduced pressure and the residue was dissolved in dichloromethane and washed twice with water. The organic phase was dried over $Na_2SO_4$ and concentrated in vacuo and the residue was purified by flash chromatography (dichloromethane/methanol 95:5) to give 27 mg (40%) of 2-(1-cyclohexyl-piperidin-4-yl)-3-oxo-2,3-dihydro-1H-isoindole-4-carboxylic acid amide.

Method B: to a solution of 2-piperidin-4-yl-2,3-dihydro-1H-isoindole-4-carboxylic acid amide hydrochloride (4.4 g, 14.8 mmol) and cyclohexanone (2.2 g, 22.45 mmol) in N,N-dimethylformamide (100 mL), glacial acetic acid (4.5 ml) and tetramethylammonium triacetoxyborohydride (11.8 g, 44.85 mmol) were added. The resulting solution was allowed to stir overnight at room temperature.

The solvent was then evaporated under reduced pressure and the resultant residue was diluted with aqueous 8% ammonia solution and extracted with ethyl acetate. The organic phase was dried with anhydrous sodium sulfate and concentrated. The crude was purified by flash chromatography (dichloromethane/methanol 95:5) and subsequently dissolved in a small amount of methanol and precipitated with diethyl ether. The precipitate was filtered and washed with diethyl ether to give 1.77 g of the desired product as a white solid (35%).

$^1$H NMR (400.5 MHz, DMSO-d$_6$) δ ppm 1.00-1.14 (m, 1H), 1.14-1.32 (m, 4H), 1.55-1.62 (m, 1H), 1.70-1.80 (m, 8H), 2.25-2.37 (m, 3H), 2.88-2.98 (m, 2H), 3.95-4.06 (m, 1H), 4.55 (s, 2H), 7.66 (br. s., 1H), 7.71 (dd, J=7.6, 7.6 Hz, 1H), 7.76 (dd, J=7.6, 1.5 Hz, 1H), 8.20 (dd, J=7.6, 1.5 Hz, 1H), 10.74 (br. s., 1H).

HRMS (ESI+): calcd. for $C_{20}H_{28}N_3O_2$ [M+H]$^+$ 342.2176; found 342.2175.

Operating according to method A, but employing suitably substituted starting material (XIV), the following compounds were obtained:

3-oxo-2-(1-pyridin-4-ylmethyl-piperidin-4-yl)-2,3-dihydro-1H-isoindole-4-carboxylic acid amide (I), cpd 8

[R=H; n=0; R1=piperidin-4-yl; m=1; R2=pyrid-4-yl]

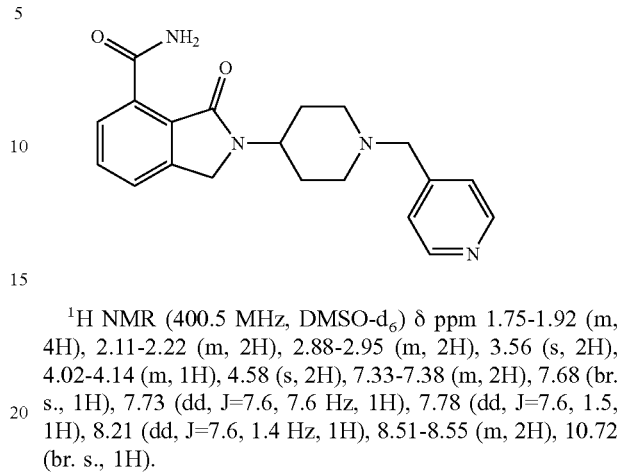

$^1$H NMR (400.5 MHz, DMSO-d$_6$) δ ppm 1.75-1.92 (m, 4H), 2.11-2.22 (m, 2H), 2.88-2.95 (m, 2H), 3.56 (s, 2H), 4.02-4.14 (m, 1H), 4.58 (s, 2H), 7.33-7.38 (m, 2H), 7.68 (br. s., 1H), 7.73 (dd, J=7.6, 7.6 Hz, 1H), 7.78 (dd, J=7.6, 1.5, 1H), 8.21 (dd, J=7.6, 1.4 Hz, 1H), 8.51-8.55 (m, 2H), 10.72 (br. s., 1H).

HRMS (ESI+): calcd. for $C_{20}H_{23}N_4O_2$ [M+H]$^+$ 351.1816; found 351.1817.

3-oxo-2-(1-thiophen-2-ylmethyl-piperidin-4-yl)-2,3-dihydro-1H-isoindole-4-carboxylic acid amide (I), cpd 9

[R=H; n=0; R1=piperidin-4-yl; m=1; R2=thiophen-2-yl]

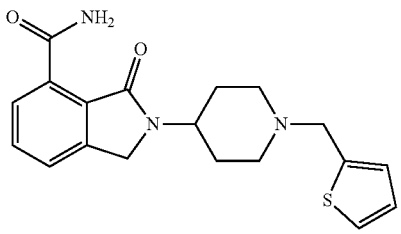

$^1$H NMR (400.5 MHz, DMSO-d$_6$) δ ppm 1.73-1.88 (m, 4H), 2.06-2.20 (m, 2H), 2.94-3.03 (m, 2H), 3.73 (s, 2H), 4.01-4.11 (m, 1H), 4.58 (s, 2H), 6.96-7.00 (m, 2H), 7.42-7.46 (m, 1H), 7.67 (br. s., 1H), 7.72 (dd, J=7.6, 7.4 Hz, 1H), 7.77 (dd, J=7.6, 1.5 Hz, 1H), 8.21 (dd, J=7.4, 1.5 Hz, 1H), 10.72 (br. s., 1H).

HRMS (ESI+): calcd. for $C_{19}H_{22}N_3O_2S$ [M+H]$^+$ 356.1427; found 356.1430.

3-oxo-2-(1-pyridin-3-ylmethyl-piperidin-4-yl)-2,3-dihydro-1H-isoindole-4-carboxylicacid amide (I), cpd 10

[R=H; n=0; R1=piperidin-4-yl; m=1; R2=pyrid-3-yl]

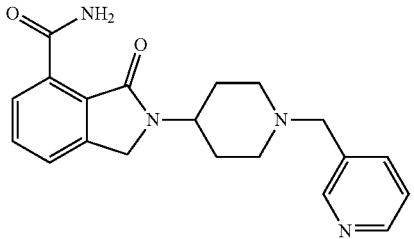 [SMILES: NC(=O)c1cccc2c1C(=O)N(C1CCN(Cc3cccnc3)CC1)C2]

$^1$H NMR (400.5 MHz, DMSO-d$_6$) δ ppm 1.70-1.80 (m, 4H), 2.08-2.18 (m, 2H), 2.87-2.96 (m, 2H), 3.55 (s, 2H), 4.01-4.12 (m, 1H), 4.56 (s, 2H), 7.37 (dd, J=7.7.4.8 Hz 1H), 7.66 (br. s., 1H), 7.71 (t, J=7.7, 7.4 Hz, 1H), 7.73 (signal overlapped by others, 1H), 7.76 (dd, J=7.7, 1.3 Hz, 1H), 8.20 (dd, J=7.4, 1.3 Hz, 1H), 8.48 (d, J=4.8 Hz, 1H), 8.52 (s, 1H), 10.71 (br. s., 1H).

HRMS (ESI+): calcd. for $C_{20}H_{23}N_4O_2$ [M+H]$^+$ 351.1816; found 351.1822.

2-(1-furan-2-ylmethyl-piperidin-4-yl)-3-ox-2,3-dihydro-1H-isoindole-4-carboxylicacid amide (I), cpd 12

[R═H; n=0; R1=piperidin-4-yl; m=1; R2=fur-2-yl]

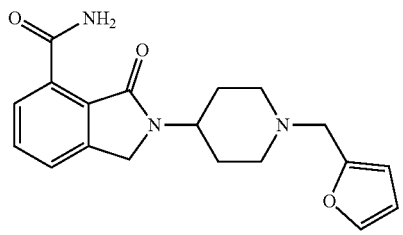 [SMILES: NC(=O)c1cccc2c1C(=O)N(C1CCN(Cc3ccco3)CC1)C2]

$^1$H NMR (400.5 MHz, DMSO-d$_6$) δ ppm 1.70-1.87 (m, 4H), 2.07-2.16 (m, 2H), 2.90-2.97 (m, 1H), 3.53 (s, 2H), 3.98-4.06 (m, 1H), 4.55 (s, 2H), 6.30 (d, J=2.4 Hz, 1H), 6.41 (dd, J=2.4, 1.8 Hz, 1H), 7.59 (br. s., 1H), 7.66 (br. s., 1H), 7.71 (dd, J=7.6, 7.4 Hz, 1H), 7.76 (dd, J=7.4, 1.3 Hz, 1H), 8.19 (dd, J=7.6, 1.3 Hz, 1H), 10.71 (br. s., 1H).

HRMS (ESI+): calcd. for $C_{19}H_{22}N_3O_3$ [M+H]$^+$ 340.1656; found 340.1651.

3-oxo-2-(1-thiophen-3-ylmethyl-piperidin-4-yl)-2,3-dihydro-1H-isoindole-4-carboxylic acid amide (I), cpd 13

[R═H; n=0; R1=piperidin-4-yl; m=1; R2=thiophen-3-yl]

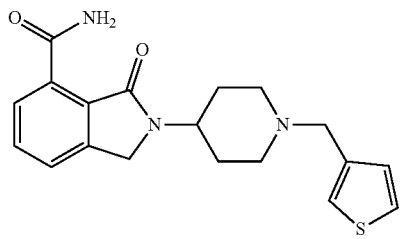 [SMILES: NC(=O)c1cccc2c1C(=O)N(C1CCN(Cc3ccsc3)CC1)C2]

$^1$H NMR (400.5 MHz, DMSO-d$_6$) δ ppm 1.72-1.90 (m, 4H), 2.00-2.12 (m, 2H), 2.90-2.99 (m, 2H), 3.53 (s, 2H), 4.00-4.09 (m, 1H), 4.57 (s, 2H) 7.08 (d, J=4.6 Hz, 1H), 7.33 (br. s., 1H), 7.49 (dd, J=4.6, 2.8 Hz, 1H), 7.67 (br. s., 1H), 7.72 (dd, J=7.6, 7.4 Hz, 1H), 7.75 (dd, J=7.6, 1.3 1H), 8.21 (dd, J=7.4, 1.3 Hz, 1H), 10.73 (br. s., 1H).

HRMS (ESI+): calcd. for $C_{19}H_{22}N_3O_2S$ [M+H]$^+$ 356.1427; found 356.1432.

2-(1-furan-3-ylmethyl-piperidin-4-yl)-3-oxo-2,3-dihydro-1H-isoindole-4-carboxylicacid amide (I), cpd 14

[R═H; n=0; R1=piperidin-4-yl; m=1; R2=fur-3-yl]

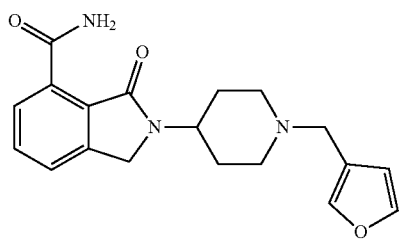 [SMILES: NC(=O)c1cccc2c1C(=O)N(C1CCN(Cc3ccoc3)CC1)C2]

$^1$H NMR (400.5 MHz, DMSO-d$_6$) δ ppm 1.72-1.89 (m, 4H), 2.02-2.12 (m, 2H), 2.90-3.02 (m, 2H), 3.37 (s, 2H), 4.00-4.10 (m, 1H), 4.56 (s, 2H), 6.45 (s, 1H), 7.58 (s, 1H), 7.62 (s, 1H), 7.67 (br. s., 1H), 7.72 (dd, J=7.6, 7.4 Hz, 1H), 7.76 (dd, J=7.4, 1.5 Hz, 1H), 8.21 (dd, J=7.6, 1.5 Hz, 1H), 10.73 (br. s., 1H).

HRMS (ESI+): calcd. for $C_{19}H_{22}N_3O_3$ [M+H]$^+$ 340.1656; found 340.1649.

3-oxo-2-(1-pyridin-2-ylmethyl-piperidin-4-yl)-2,3-dihydro-1H-isoindole-4-carboxylic acid amide (I), cpd 15

[R═H; n=0; R1=piperidin-4-yl; m=1; R2=pyrid-2-yl]

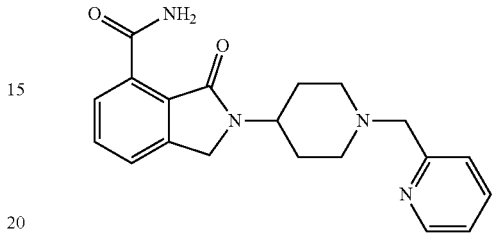

$^1$H NMR (400.5 MHz, DMSO-d$_6$) δ ppm 1.74-1.93 (m, 4H), 2.12-2.28 (m, 2H), 2.91-3.00 (m, 2H), 3.65 (s, 2H), 4.02-4.13 (m, 1H), 4.58 (a, 2H), 7.28 (dd, J=6.8, 4.8 Hz, 1H), 7.47 (d, J=7.8 Hz, 1H), 7.67 (br. s., 1H), 7.73 (dd, J=7.4, 7.4 Hz, 1H), 7.76-7.83 (m, 2H), 8.21 (dd, J=7.4, 1.3 Hz, 1H), 8.51 (d, J=4.8 Hz, 1H), 10.73 (br. s., 1H).

HRMS (ESI+): calcd. for $C_{20}H_{23}N_4O_2$ [M+H]$^+$ 351.1816; found 351.1815.

3-oxo-2-[1-(1H-pyrrol-2-ylmethyl)piperidin-4-yl]-2,3-dihydro-1H-isoindole-4-carboxylic acid amide (I), cpd 16

[R═H; n=0; R1=piperidin-4-yl; m=1; R2=1H-pyrrol-2-yl]

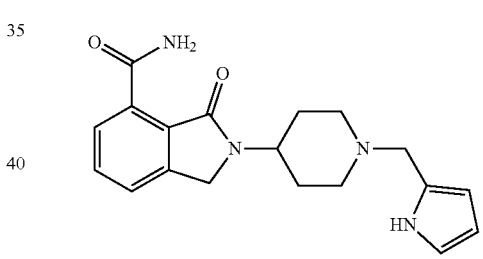

$^1$H NMR (400.5 MHz, DMSO-d$_6$) δ ppm 1.70-1.88 (m, 4H), 1.96-2.09 (m, 2H), 2.88-2.99 (m, 2H), 3.44 (s, 2H), 3.94-4.09 (m, 1H), 4.55 (s, 2H), 5.89 (br. s., 1H), 5.94 (br. s., 1H), 6.65 (br. s., 1H), 7.67 (br. s., 1H), 7.72 (dd, J=7.6, 7.4 Hz, 1H), 7.77 (dd, J=7.6, 1.3 Hz, 1H), 8.20 (dd, J=7.4, 1.3 Hz, 1H), 10.65 (br. s., 1H), 10.73 (br. s., 1H).

HRMS (ESI+): calcd. for $C_{19}H_{23}N_4O_2$ [M+H]$^+$ 339.1816; found 339.1812.

2-(1-cyclopropylmethyl-piperidin-4-yl)-3-oxo-2,3-dihydro-1H-isoindole carboxylic acid amide (I), cpd 24

[R═H; n=0; R1=piperidin-4-yl; m=1; R2=cyclopropyl]

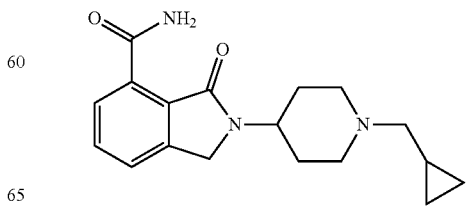

¹H NMR (400.5 MHz, DMSO-d₆) δ ppm 0.06-0.12 (m, 2H), 0.44-0.50 (m, 2H), 0.80-0.89 (m, 1H), 1.72-1.88 (m, 4H), 2.00-2.11 (m, 2H), 2.21 (d, J=6.3 Hz, 2H), 3.04-3.13 (m, 2H), 3.98-4.09 (m, 1H), 4.56 (s, 2H), 7.66 (br. s., 1H), 7.72 (dd, J=7.6, 7.6 Hz, 1H), 7.77 (dd, J=7.6, 1.2 Hz, 1H), 8.20 (dd, J=7.6, 1.2 Hz, 1H), 10.73 (br. s., 1H).

HRMS (ESI+): calcd. for $C_{18}H_{24}N_3O_2$ [M+H]⁺ 314.1863; found 314.1860.

The invention claimed is:

1. A pharmaceutical composition comprising:
a therapeutically effective amount of a compound selected from the group consisting of: 2-(1-cyclohexyl-piperidin-4-yl)-3-oxo-2,3-dihydro-1H-isoindole-4-carboxylic acid amide; and 2-(1-cyclohexyl-piperidin-4-yl)-6-fluoro-3-oxo-2,3-dihydro-1H-isoindole-4-carboxylic acid amide; or a pharmaceutically acceptable salt thereof,
at least one pharmaceutically acceptable excipient, carrier or diluent, and
one or more chemotherapeutic agent.

2. The pharmaceutical composition according to claim 1, wherein said one or more chemotherapeutic agent is an alkylating agent.

3. The pharmaceutical composition according to claim 1, wherein said one or more chemotherapeutic agent is temozolomide.

4. A method of treating a cancer mediated by PARP-1 protein comprising the simultaneous, separate or sequential administration as a combined preparation of a product comprising:
a. a compound selected from the group consisting of: 2-(1-cyclohexyl-piperidin-4-yl)-3-oxo-2,3-dihydro-1H-isoindole-4-carboxylic acid amide; and 2-(1-cyclohexyl-piperidin-4-yl)-6-fluoro-3-oxo-2,3-dihydro-1H-isoindole-4-carboxylic acid amide, or a pharmaceutically acceptable salt thereof; and
b. one or more chemotherapeutic agents.

5. The method according to claim 4, wherein said one or more chemotherapeutic agent is an alkylating agent.

6. The method according to claim 4, wherein said one or more chemotherapeutic agent is temozolomide.

* * * * *